US006234793B1

(12) United States Patent
Brattesani et al.

(10) Patent No.: US 6,234,793 B1
(45) Date of Patent: May 22, 2001

(54) TEXTURED DENTAL MATRIX BANDS AND RELATED METHODS

(75) Inventors: Steven J. Brattesani, San Francisco, CA (US); Dan E. Fischer, Sandy, UT (US)

(73) Assignee: Ultradent Products, Inc., Sandy, UT (US)

(*) Notice: Subject to any disclaimer, the term of this patent is extended or adjusted under 35 U.S.C. 154(b) by 0 days.

(21) Appl. No.: 09/503,689

(22) Filed: Feb. 14, 2000

Related U.S. Application Data

(63) Continuation-in-part of application No. 09/356,629, filed on Jul. 19, 1999, now abandoned.

(51) Int. Cl.[7] .................................................. A61C 7/00
(52) U.S. Cl. ................................................ 433/39; 433/149
(58) Field of Search ........................... 433/39, 40, 149, 433/155

(56) References Cited

U.S. PATENT DOCUMENTS

| | | |
|---|---|---|
| 532,722 | 1/1895 | Dennis . |
| 2,502,903 | 4/1950 | Tofflemire . |
| 2,686,970 | 8/1954 | Reiter . |
| 2,687,573 | 8/1954 | Stone . |
| 2,709,302 | 5/1955 | Reiter . |
| 2,722,746 | 11/1955 | Brenner . |
| 2,749,616 | 6/1956 | Curry . |
| 3,425,125 | 2/1969 | Bergendal . |
| 3,516,162 | 6/1970 | Ainsworth . |
| 3,890,714 | * 6/1975 | Gores .................................. 433/149 |
| 3,908,273 | 9/1975 | Reiter . |
| 4,563,152 | 1/1986 | McClure .............................. 433/39 |
| 4,631,030 | * 12/1986 | von Weissenfluh ................. 433/149 |
| 4,696,646 | * 9/1987 | Maitland ............................. 433/149 |
| 4,704,087 | 11/1987 | Dragan ................................ 433/39 |
| 4,824,365 | 4/1989 | von Weissenfluh ................. 433/40 |
| 4,915,627 | 4/1990 | Hirdes ................................. 433/155 |
| 5,055,045 | 10/1991 | Dickie et al. ....................... 433/155 |
| 5,248,258 | * 9/1993 | Feldman .............................. 433/39 |
| 5,330,353 | * 7/1994 | Wavrin ................................ 433/39 |
| 5,342,197 | 8/1994 | Stein et al. .......................... 433/155 |
| 5,421,725 | 6/1995 | von Weissenfluh ................. 433/149 |
| 5,501,595 | * 3/1996 | Brorson ............................... 433/39 |
| 5,626,475 | 5/1997 | Von Weissenfluh et al. ....... 433/155 |
| 5,743,738 | 4/1998 | Baffelli et al. ...................... 433/149 |
| 5,890,900 | 4/1999 | Fischer et al. ...................... 433/149 |
| 5,890,901 | 4/1999 | Fischer et al. ...................... 433/149 |

FOREIGN PATENT DOCUMENTS 2603130    8/1977  (DE) .

* cited by examiner

Primary Examiner—Ralph A. Lewis
(74) Attorney, Agent, or Firm—Workman, Nydegger & Seeley

(57) ABSTRACT

The present invention relates to a dental matrix band used during tooth restoration procedures. The matrix bands have a smooth interior side which is placed in contact with the tooth requiring restoration. The exterior side a frictional engagement surface which is at least a portion of its surface that is configured to provide increased friction. Such a matrix band is placed around a tooth to be restored with the frictional engagement surface facing the embrasure or space between the teeth. A dental wedge can then be inserted into the embrasure against the frictional engagement surface to hold the dental matrix band stationary with respect to the tooth being restored. The frictional engagement surface is sufficiently rough that dental wedges are much less likely to slip out of an embrasure once positioned against the frictional engagement surface, thereby ensuring that a matrix band will be securely held in place by a dental wedge to enable the practioner to confidently proceed with the restoration. The matrix bands may be formed from opaque materials such as stainless steel or from materials which are at least translucent.

50 Claims, 23 Drawing Sheets

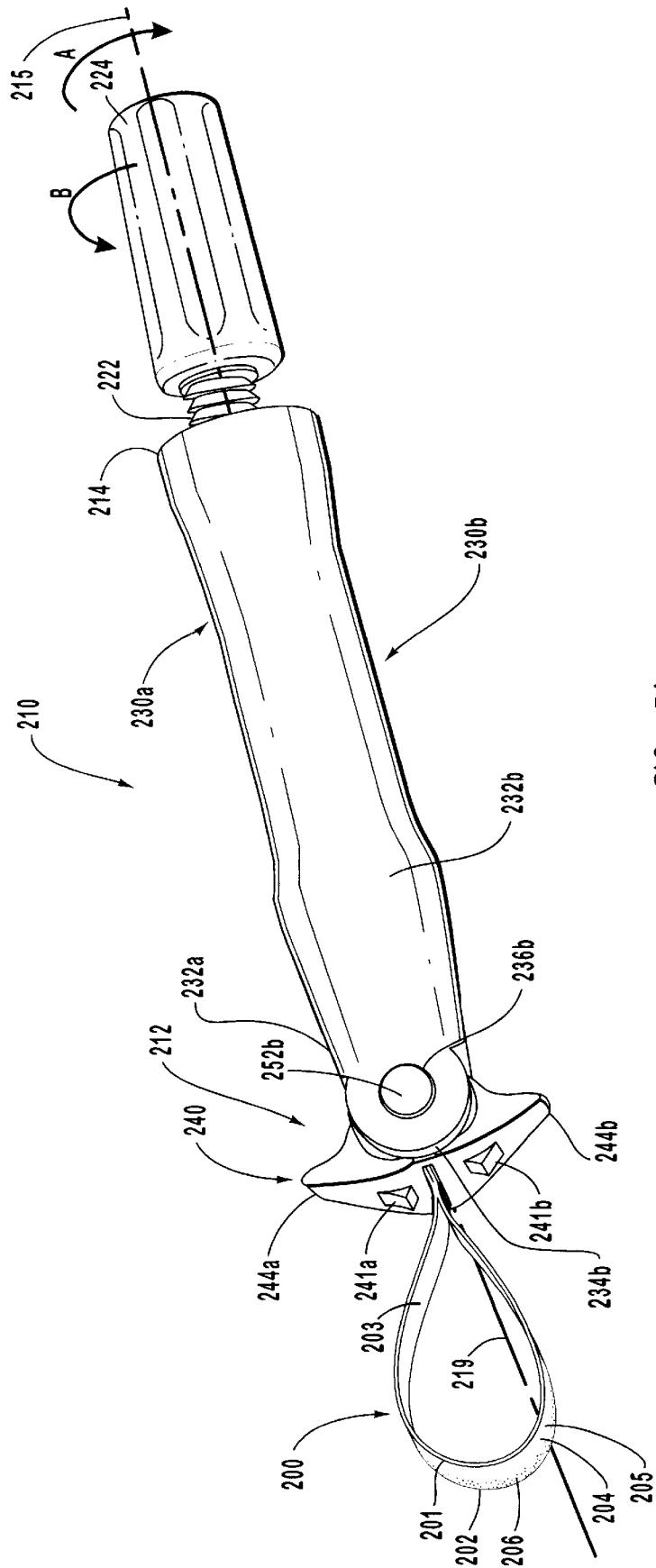

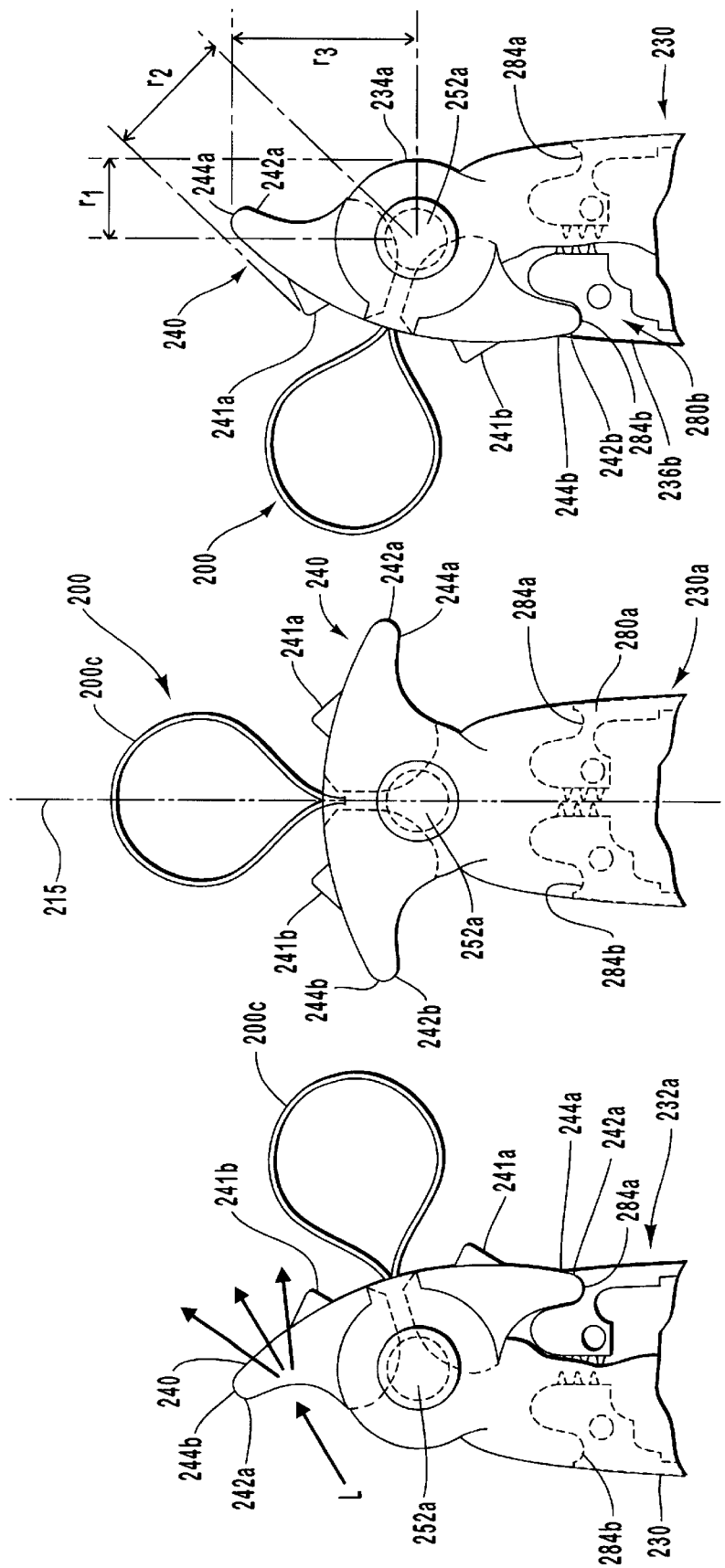

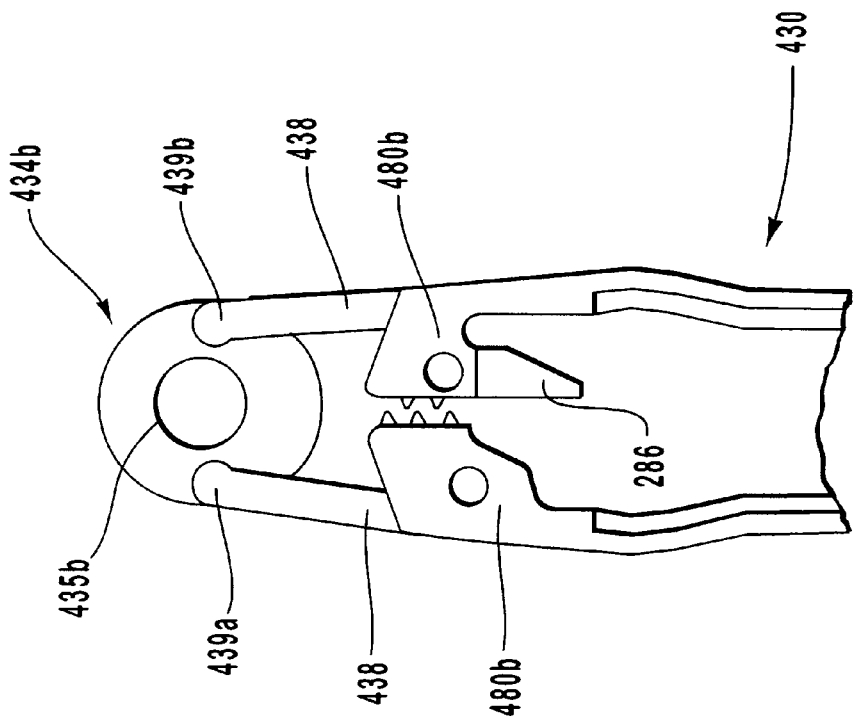
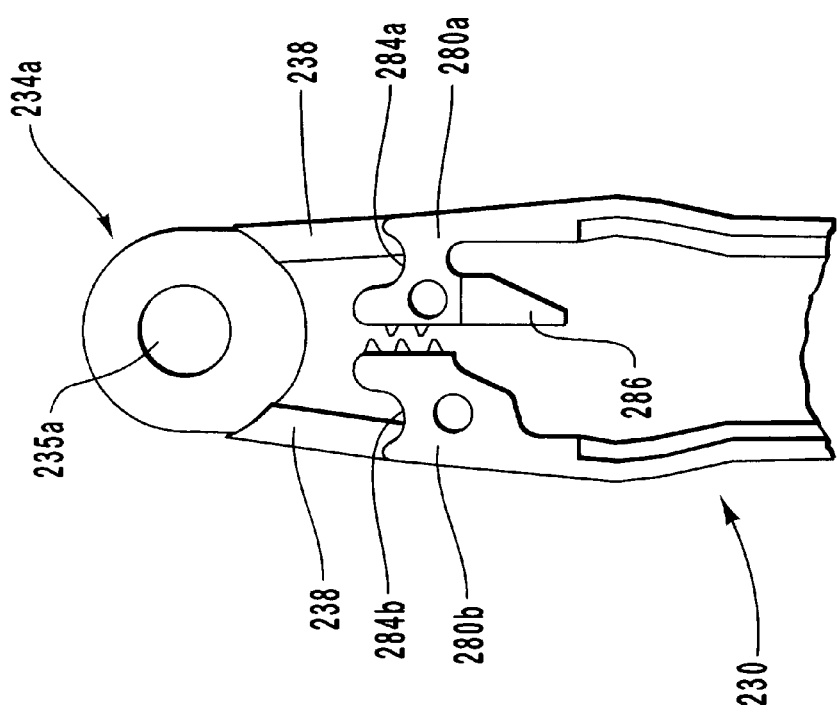

TEXTURED DENTAL MATRIX BANDS AND RELATED METHODS

This application is a continuation-in-part patent application of U.S. patent application Ser. No. 09/356,629, now abandoned, entitled Dental Matrix Retainer Clamps with Improved Visibility which was filed on Jul. 19, 1999 on behalf of Dan E. Fischer. Ser. No. 09/356,629, now abandoned, is incorporated herein by specific reference.

BACKGROUND

1. Field of the Invention

The inventions disclosed herein are in the field of dental instruments. More particularly, the inventions relates to dental matrix bands which are positioned around a dental preparation to act as a form for the material used to fill the preparation. The inventions also relate to the use of such bands in band holders as well as the related methods.

2. Background Art

In the field of dentistry, dental practitioners often treat patients who have developed cavities on the side of a tooth. When these cavities are located adjacent to neighboring teeth they are known as interproximal cavities. In order to treat cavities on the sides of teeth such as interproximal cavities, the dental practitioner removes the infected portion of the tooth, then deposits a filling such as a resinous material or an amalgam into the tooth preparation.

In order to properly deposit the filling without undesired seepage of the filling material beyond the side of the tooth, typically a matrix band is disposed about the tooth, after which the filling material is deposited. A matrix band is typically a metallic or plastic strip having first and second ends which are joined, thereby forming a mold which is disposed about the tooth. When encircled about the tooth, the matrix band acts as a form, similar in function to a concrete form, providing a mold for the desired shape of the repaired tooth.

In order to maintain the matrix band in a desired position with respect to the tooth to be repaired, small dental wedges are often placed in the interproximal spaces between the matrix band and the teeth adjacent the tooth to be repaired. The wedges also space the teeth adjacent to the tooth to be repaired during the filling procedure. Dental wedges may be used to spread adjacent teeth for a variety of other purposes such as enabling a dental matrix band to be initially positioned around a tooth. Due to the elasticity of the periodontal fibers the teeth will resume their original position after the wedges and matrix bands are removed.

FIG. 1 depicts a tooth 10 encircled by a dental matrix band 20. A dental wedge 30 is shown being positioned between tooth 10 and adjacent tooth 12. Pliers 18 are used to hold wedge 30. FIG. 2 shows a typical matrix band at 20 before being placed around a tooth. FIG. 3 shows dental wedge 30 in more detail.

Matrix bands are sold having many different shapes, thickness and properties. For example, different matrix bands are sold for use with molars, premolars or bicuspids, etc. of adults as well as specialized pediatric matrix bands. One of the commonly used matrix band configurations is known as the Tofflemire-type matrix band, such as is shown in FIG. 2. Tofflemire-type matrix bands are elongated strips which are slightly curved or arched such that the bands are shaped somewhat like a boomerang. Matrix bands are also available which are straight and can therefore be sold in spools. Many matrix bands also have a lip or cervical extension to assist in placing the band past the cervical margin.

The matrix bands have any suitable thickness to fit between teeth. However, typical thickness are 0.03 mm, 0.035 mm, 0.038 mm, 0.045, and 0.05 mm. Generally, contact is optimized by using the thinnest matrix band possible especially when polymerization of a composite is required. Some matrix bands are sold which have regions, known as contact areas, which are much thinner than the remainder of the matrix band. For example, the contact area may be 0.0127 mm (0.0005 inches thick) while the remainder is 0.03 mm thick or greater. Such matrix bands are particularly useful with Class II restorations.

The matrix bands can also be formed from different materials to yield different properties. Traditionally, matrix bands have been prepared from stainless steel. Bands can be designed to be adequately soft to allow them to be individually shaped by finger pressure or by an instrument while others are more rigid. Such properties can be achieved by varying the thickness or the composition of the band. Increasing amounts of matrix bands are being sold which are transparent or translucent to enable radiant energy to pass through the band toward composite material in a preparation to polymerize the composite material. Such bands may be integrally formed from a single material such as polyester or Mylar™ sold by DuPont. Additionally, bands are sold with portions formed from translucent plastic and other portions which are formed from stainless steel. One of the advantages of matrix bands formed from both stainless steel and plastic is that the stainless steel can pass through tight contact points which are sometimes difficult for some plastics.

Many matrix band designs have been produced to achieve various objectives. For example, U.S. Pat. No. 4,563,152 discloses the ability to use a matrix band to replace a narrow sand paper strip used to remove "flash" which forms due to overfilling a tooth with a polymerizable composite material. It was observed that the sanding strip was generally thicker than the matrix band so it was difficult to insert and successfully use the sanding strip. The solution to this problem disclosed in U.S. Pat. No. 4,563,152 is the use of a matrix band which has a portion on the side which faces the preparation which is configured to abrade the flash and other excess cured material that has escaped the cavity preparation. This enabled the matrix band to be used for its conventional purpose and also to abrade the restorative material from the mesial surface of the restored tooth without having to remove the band and insert the sanding strip.

A significant problem with the use of conventional matrix bands and dental wedges is the tendency of the dental wedges to slip out their positions in the interproximal spaces. When the wedges slip out from between the teeth, the desired configuration of the restored tooth may be distorted. Another problem related to the interface between wedges and dental matrix bands is the potential for injurious slippage during insertion of a wedge. These problems are not solved by the prior art.

In addition to the prior art wedge shown in FIG. 3, FIGS. 4–5 depict other examples of prior art wedges respectively at 40 and 50 and are discussed hereinbelow. Typical wedges have a triangular cross section as shown. This triangular cross section includes a thin apex at the distal insertion end which widens into a flat base at the other end, the proximal gripping end. Each wedge in FIGS. 3–5 is depicted as having a distal insertion end, respectively shown at 32, 42 and 52 and a proximal gripping end, shown respectively at 34, 44 and 54.

As shown in FIG. 1, a wedge is typically placed with the widened end located toward the gum line and with the thin apex extending between the teeth and away from the gums in order to fit properly in an interproximal space. When using such dental wedges, the practioner is careful to orient the wider end toward the gumline while the more thinner, pointed apex is directed upward between the teeth.

In light of this triangular configuration of typical wedges, it is important to orient the wedge properly with respect to the interproximal space before pressing the body of the wedge, shown respectively in FIGS. 3–5 at 36, 46 and 56, into the interproximal space. In addition, the properly oriented wedge must be precisely guided into the space. However, it is often difficult to orient the wedges correctly within the desired interproximal space in the mouth due to their small size and the difficulty involved in controlling the insertion of the wedge without making the patient uncomfortable or possibly damaging the gums and/or teeth of the patient. Accordingly, a practioner maintains a solid grip on the wedge in order to strategically align and properly guide the wedge. Of course, it is also necessary for the practitioner to maintain a solid grip on the wedge to avoid dropping the wedge.

The tendency of these wedges to slip due to their shape is further increased due to their smoothness and relative rigidity when tightly gripped, particularly when covered with fluids, such as saliva or blood. Such smoothness and rigidity inherently result from the type of materials used to form conventional wedges. Typical dental wedges are comprised of a rigid plastic or wood, such as that from sycamore trees, having a smooth exterior surface which compounds the difficulties associated with firmly gripping the wedges due to their small size. Note that wedge 30 is formed from wood while wedge 40 is formed from a translucent plastic.

A practitioner typically uses small-nosed pliers, known as cotton pliers, to grip a particular wedge and to position the wedge within the mouth. To enhance a practioner's ability to grasp a wedge, some wedges have a head disposed on the proximal end of the body of the wedge. For example, wedges 40 and 50, are shown respectively with heads 48 and 58 attached to bodies 46 and 56. Head 48 has four gripping surfaces, 49a–d, which makes it easier to grasp than head 58. However, since head 48 is typically comprised of a rigid material, such as plastic, pliers still readily slip when contacting such wedges.

After the wedge is initially positioned, the dentist forces the wedge into final position. During the forced insertion, the likelihood of injury is greatest as the pliers or tweezers may slip off the wedge into the soft tissues in a patient's mouth. Additionally, when the dentist attempts to regrasp the wedge with cotton pliers there is also risk of slipping off the wedge. The slippery nature of the wedge can cause the wedge to be lost within the patients' mouth or ejected from the pliers across the room. Even if the small wedge is found, often it cannot be utilized due to the likelihood of contamination.

As indicated above, the slippery nature of wedges combined with the conditions in the oral cavity sometimes enable the wedges to become dislodged after being positioned in an interproximal space. The tendency to be displaced after being positioned may also result from being used in very tight interproximal spaces which makes it difficult to insert a sufficiently significant portion of the body of the wedge into the space.

There is, therefore, a need in the art for a matrix band which minimizes the tendency of wedges to be displaced from an interproximal spaces after being positioned therein such that the risk is reduced of impacting the desired shape of a restored tooth due to slippage.

BRIEF SUMMARY AND OBJECTS OF THE INVENTION

It is therefore an object of the invention to provide an improved dental matrix band.

It is another object of the invention to provide a dental matrix band which enables a dental wedge to be inserted and securely held.

Additionally, it is another object of the invention to provide a dental matrix band which minimizes the tendency of wedges to slip out from an interproximal space after being placed therein adjacent to the dental matrix band.

Finally, it is another object to provide dental matrix band holders preloaded with a dental matrix band capable of being positioned around a tooth and enabling a dental wedge to remain in place to hold the dental matrix band stationary with respect to a tooth requiring restoration.

These objects are achieved by unique features of the present invention. Matrix bands are disclosed herein which have a smooth interior side which is placed in contact with the tooth requiring restoration. The exterior side has at least a portion of its surface configured to provide increased friction. The portion which provides increased friction is referred to herein as a frictional engagement surface. The matrix band is positioned around the tooth requiring restoration such that the frictional engagement surface faces the embrasure or space between the teeth. A dental wedge can then be inserted into the embrasure against the dental wedge to hold the dental matrix band stationary with respect to the tooth being restored. The frictional engagement surface is sufficiently textured or rough that dental wedges are much less likely to slip out of an embrasure once positioned against the frictional engagement surface. The increased resistance provided by the frictional engagement surfaces ensure that a matrix band will be securely held in place by a dental wedge. This enables the practioner to confidently proceed with the restoration.

The matrix bands may be formed from opaque materials such as stainless steel or the matrix bands may be formed from material which are transparent or translucent. Matrix bands which are at least translucent also preferably resemble metal in its tensile and fluctural qualities. The matrix bands may also have a portion formed from metal with the remainder being formed from a plastic material that is at least relatively clear.

The unique matrix bands can be utilized with conventional matrix band holders or unique matrix band holders as disclosed herein. The unique dental matrix retainer clamps facilitate both visibility for the dental professional within a patient's mouth and more rapid and efficient curing of light-curable composite materials, and a secure configuration during a dental procedure. The inventive dental matrix retainer clamp, in one embodiment, provides a head element that is substantially translucent such that the degree of any shadow that may be cast upon a patient's tooth, whether as a hindrance to the dental professional's visibility or as a hindrance to efficiently conveying a curing light beam onto the patient's tooth, is substantially reduced. In another preferred embodiment of the present invention, the dental matrix retainer clamp has a profile that is significantly reduced compared to the profile of devices used in the prior art. Thereby, visibility for the dental professional and/or an unobstructed curing light beam onto the restorative material during the curing process is facilitated.

The unique matrix bands can also be utilized with conventional dental wedges or unique dental wedges as disclosed herein. The unique dental wedges are more easily gripped, placed and removed than conventional dental wedges. One embodiment of the unique dental wedges relates to a dental wedge, comprising: (i) a body having a proximal end and a distal end; and (ii) a head coupled to the body which has more than four different flat sides extending about the circumference of the head to serve as gripping or bracing surfaces. The head preferably has six, eight or more different flat gripping surfaces. The number of flat gripping surfaces provide many angles and positions from which the practitioner can grasp the dental wedge. A practitioner is thus more likely to achieve a grip which will sufficiently hold the wedge. The head may also have an elastomeric cap which compresses when a dental instrument is urged against the cap to push the wedge into position between two teeth.

In another embodiment, a neck couples the head to the body which has a smaller diameter than the adjacent portion of the head or body. The neck provides a groove in which tweezers or pliers may be disposed, allowing the practitioner to more readily grip the wedge. Accordingly, the practitioner can optionally firmly grasp the neck, push within the groove against the body to place a wedge in a patient's mouth or pull against the head to remove the wedge while a dental instrument remains stable and is securely within the groove. The neck preferably includes a plurality of different flat gripping surfaces extending about the circumference of the neck for disposition of the tweezers or pliers thereon. The flat gripping surfaces of the neck provide additional positions from which a practitioner is able to grasp the wedge. To dramatically increase the number of positions from which a practitioner is able to grasp the wedge, the flat gripping surfaces of the head may be offset with respect to the flat gripping surfaces of the neck.

These and other objects, features and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which:

FIG. 7A is a perspective view of the dental matrix retainer clamp of the present invention.

FIG. 9A is a top plan view of the dental matrix retainer clamp shown in FIGS. 7A–7D with the head element in a first locked position.

FIG. 9B is a top plan view of the dental matrix retainer clamp shown in FIGS. 7A–7D with the head element in an intermediate position.

FIG. 9C is a top plan view of the dental matrix retainer clamp shown in FIGS. 7A–7D with the head element is a second locked position.

FIGS. 13 and 14 are top plan cut-away views revealing half of the main body element of the dental matrix retainer clamp to illustrate a difference in structure between two embodiments of the invention. FIG. 14 illustrates a main body element flange protruding portion that is an extension of the main body element wall onto the flange portion and that is configured to engage the head element detent portions of the head element depicted in FIGS. 12A–D.

DETAILED DESCRIPTION OF THE PREFERRED EMBODIMENTS

Figure 1:
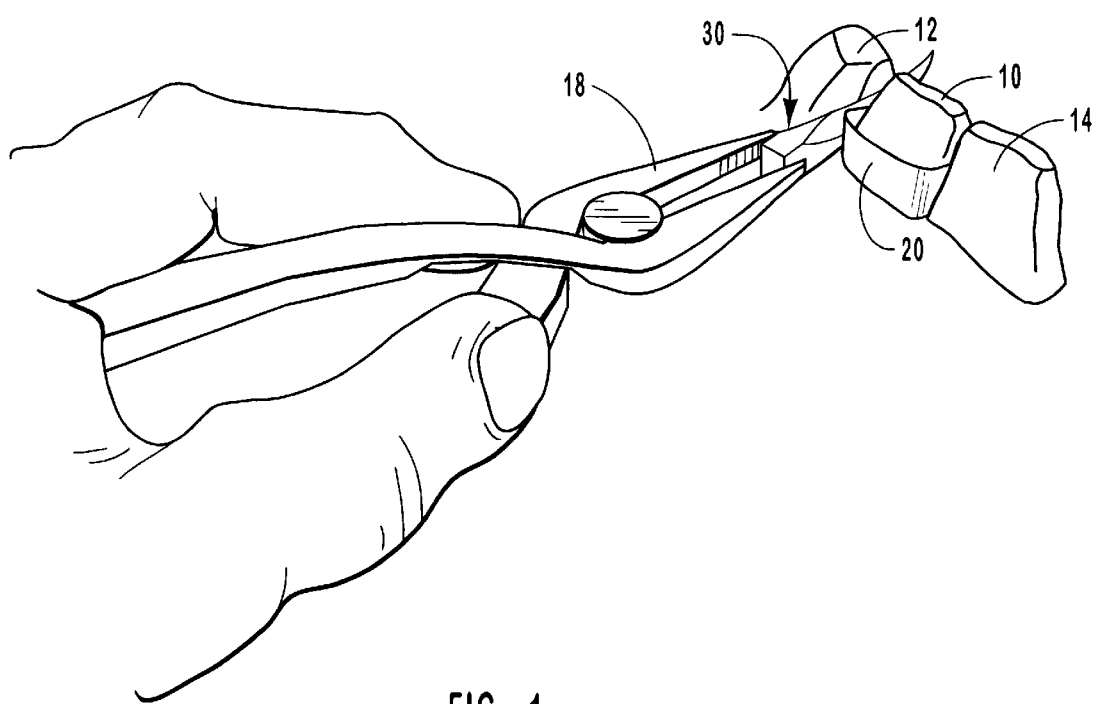
FIG. 1 is a perspective view of a user's hand pushing a conventional dental wedge with pliers between the teeth and against a matrix band.
Figure 2:
FIG. 2 is a perspective view of a conventional dental matrix band.

The matrix band of the present invention is useful for engagement with a dental wedge to maintain the matrix band in a desired orientation during restoration of a tooth. As set forth hereinbelow, the matrix band can have various configurations and can be used with conventional dental wedges and matrix band clamps or holders as well as inventive dental wedges and matrix band clamps.

The matrix bands of the present invention are flexible strips configured such that the side of the matrix band which is placed in contact with the tooth is preferably smooth while the other side has at least a portion of its surface which provides increased friction. The portion which provides increased friction is referred to herein as a frictional engagement surface. The frictional engagement surface is sufficiently textured or rough that dental wedges are much less likely to slip out of an embrasure once positioned against the frictional engagement surface. The increased resistance provided by the frictional engagement surfaces ensures that a matrix band will be securely held in place by a dental wedge. Accordingly, a practioner can securely proceed with a restoration.

The side of the matrix band facing the tooth being restored is preferably smooth to enable the matrix band to come into as close of contact as possible with the tooth surfaces. This close contact enables the restoration to be most ideally formed. If both sides are configured to provide friction then the interior side, the side facing the tooth to be restored may negatively impact the shape of restoration. Additionally, the interior side is preferably smooth as it makes placement of the matrix band easier. More particularly, since the frictional engagement surface is configured to provide increased friction it also results in increased frictional resistance during placement. This increased frictional resistance during placement is offset by the smooth surface of the interior surface. In addition to facilitating the placement of the matrix band and the formation of a smooth filling, the smooth interior side also facilitates easy removal of the matrix band after completion of the dental procedure.

FIGS. 6A–6M depict various designs of dental matrix bands configured in accordance with the present invention shown respectively at 100a–100m. Each dental matrix band 100a–100l has a top edge 101 opposite a bottom edge 102. The interior side of the matrix bands 100a–100m, shown only in FIG. 6L, at 103l has a smooth surface to be engaged against a tooth requiring restoration. Each exterior side 104a–m of matrix bands 100a–m is shown having a surface 105 which is at least partially a frictional engagement surface 106 adapted to provide frictional engagement with a dental wedge. The frictional engagement surfaces are described in detail hereinbelow.

Like most conventional dental matrix bands, dental matrix bands 100a–l are slightly curved or arched such that the bands are shaped somewhat like a boomerang. More particularly, midsection 114 is arched such that when the two opposite ends, first end 112 and second end 116 are brought together then midsection 114 is slanted. The midsection 114 is slanted such that top edge 101 extends out farther than bottom edge 102. This configuration enables the matrix bands to be easily adapted to the shape of the tooth requiring restoration. While matrix bands 100a–l are slightly curved, the matrix bands may also be straight like matrix band 100m shown in FIG. 6M which is provided on a spool shown at 140. Note also that dental matrix band 100a–k are configured to be sold as flat bands ready for the practioner to shape while dental matrix band 100l is already preshaped.

As mentioned above, each matrix band 100a–m has a frictional engagement surface 106a–m on the respective exterior sides 104a–m. The frictional engagement surfaces is preferably formed by sandblasting the matrix band. However, the frictional engagement surface can be formed by any suitable process. For example, the frictional engagement surface may be formed by microetching the exterior side or a portion of the exterior side of the matrix band. Roughening the exterior side of the matrix band by sandblasting or microetching is the preferred method for forming a frictional engagement surface as this also reduces the thickness of the matrix band in that region.

Although a roughened frictional engagement surface is the preferred frictional engagement surface, frictional engagement surfaces formed by other methods may be useful in some circumstances. An example of such a method for forming a frictional engagement surface involves adhering abrasive material to the exterior side of the matrix band or a portion thereof, preferably through electrostatic methods. This method is less preferred as the adhered abrasive material increases the thickness of the matrix band. The frictional engagement surface may also be a sticky portion of the exterior side. Such a sticky portion may be formed, for example, by application of a suitable adhesive to the exterior side of the matrix band. Some frictional engagement surfaces may also be formed by molding such that the frictional engagement surface is formed during the molding process. While such a frictional engagement surface may a uniform pattern such as a series of ridges or a criss-cross knurled configuration, it may also be designed to appear to have been sandblasted.

As discussed above, some processes used to form a frictional engagement surface, such as a sandblasting process or an etching process, involve the removal of parts of the matrix band which decreases the thickness of the matrix band at the frictional engagement surface. The relative thinness of the portion configured with a frictional engagement surface compared to the remainder of the matrix band may enable the matrix band to be more easily positioned. More particularly, since the abrasive nature of the frictional engagement surface may increase the difficulty experienced in moving the matrix band within an embrasure, the relative thinness may compensate for the increased friction caused by the frictional engagement surface. For this reason, sandblasting and etching process as well as any other process which creates a textured or roughened surface through the removal of parts of the matrix band are preferred over those which increase the thickness such as adhering abrasive material onto the matrix band. Additionally, roughened surfaces are less likely to have any loose debris as may be the case with adhered abrasive materials.

Many different matrix band configurations are shown in FIGS. 6A–6M. Matrix band 100a is depicted as having a frictional engagement surface 106a extending from bottom edge 102a upward toward top edge 101a at least one-third of the distance between bottom edge 102a and top edge 101a. The remainder of the surface 105a of exterior side 104a is relatively smooth. Matrix band 100b has a different design than matrix 100a but has a similar one-third portion adapted to provide frictional engagement with a dental wedge. Matrix band 100c is included to show that the frictional engagement surface may be a continuous strip like that of frictional engagement surfaces 106a and 106b but it may cover a different amount of exterior side 104c. All of the exterior side 104d of the matrix band 100d is a frictional engagement surface. Similarly, all of the exterior side of matrix band 104e is a frictional engagement surface.

The frictional engagement surface need not occur along the entire length of the matrix band as shown in FIGS. 6F–6I and 6K. The frictional engagement surface can be localized as needed so that only the portion of the matrix band which will be eventually positioned in an embrasure is adapted to engage a dental wedge. Essentially, the frictional engagement surface can be located anywhere need depending on the particular matrix band design.

Figure 6A:
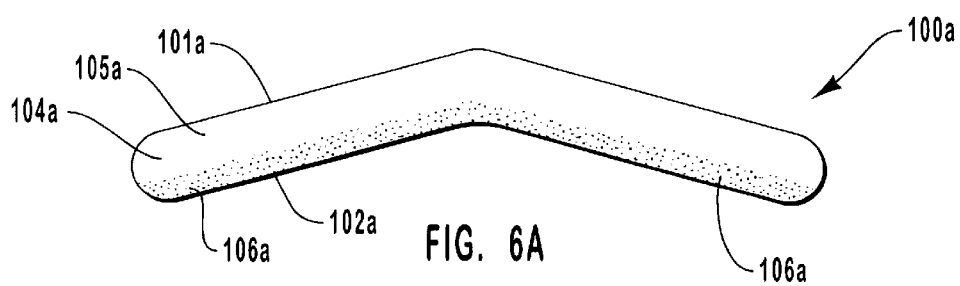
FIGS. 6A–M are views of the dental matrix bands of the present invention.
Figure 6B:
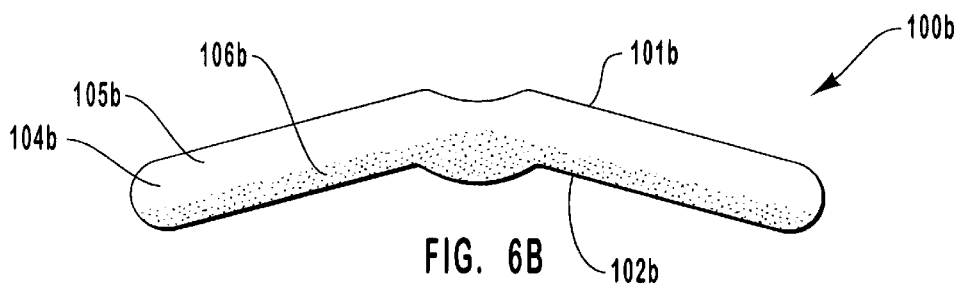
Figure 6C:
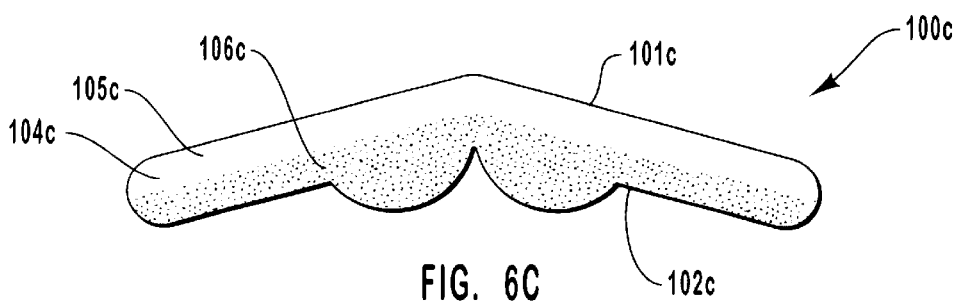
Figure 6D:
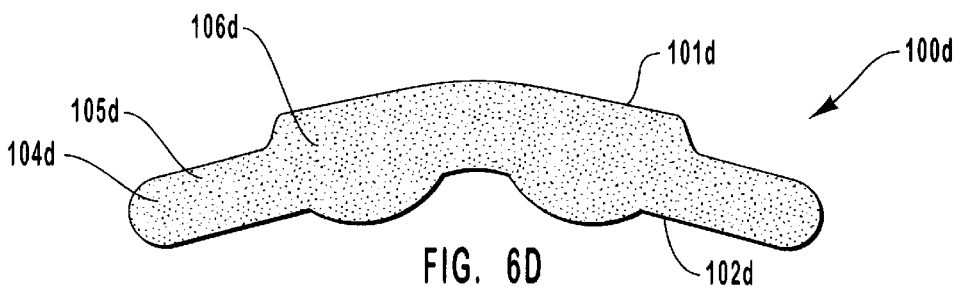
Figure 6E:
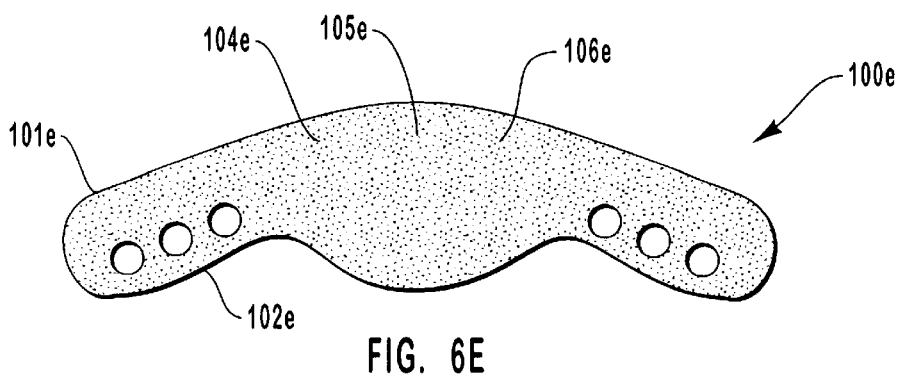
Figure 6F:
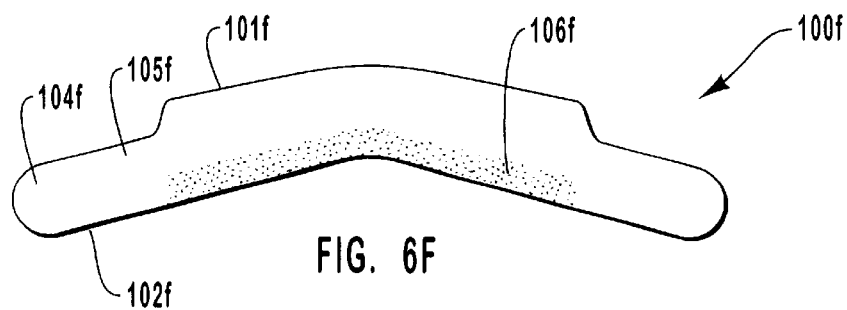
Figure 6G:
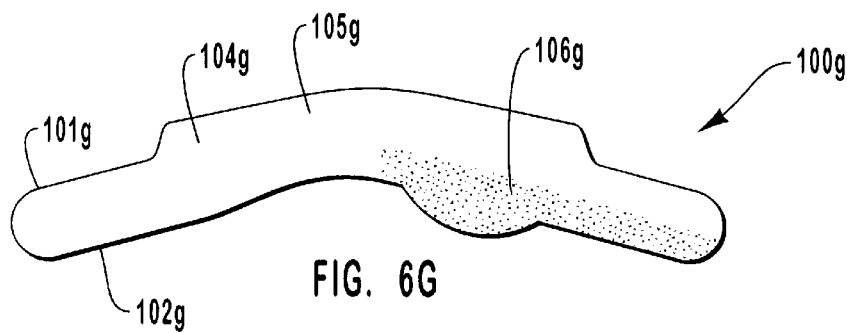
Figure 6H:
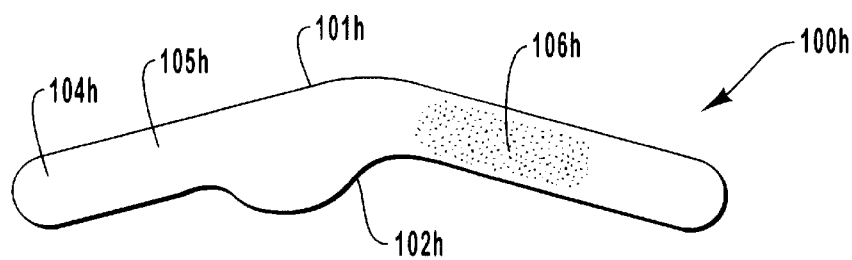
Figure 6I:
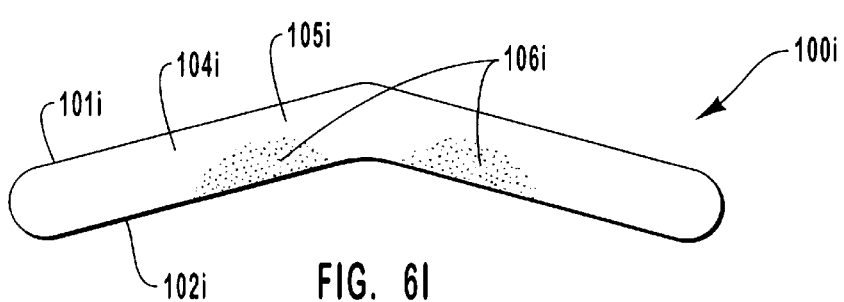
Figure 6J:
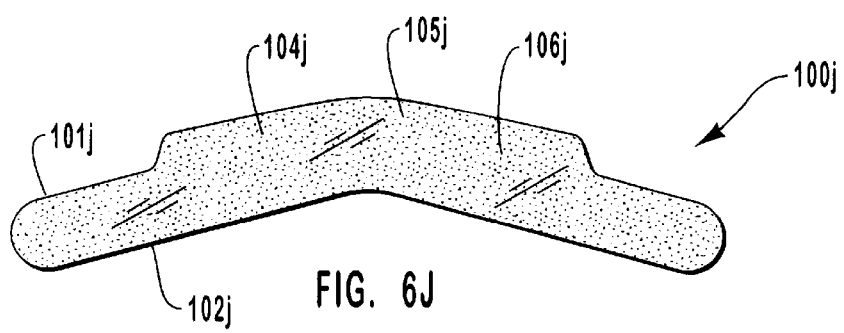
Figure 6K:
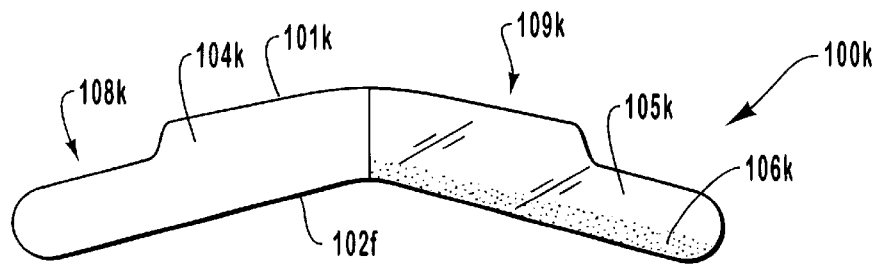
Figure 6L:
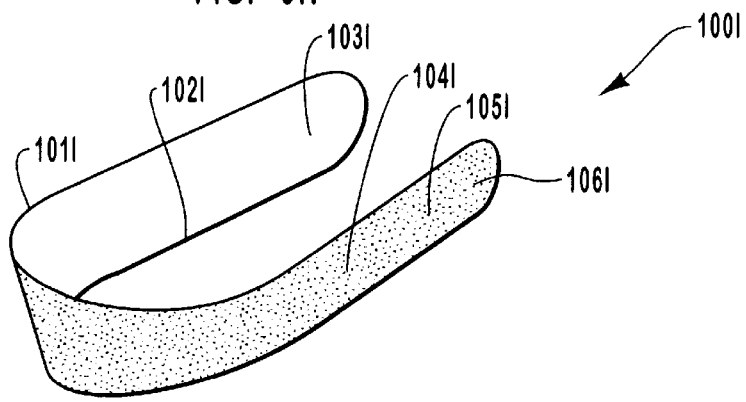

Matrix bands 100j and 100j are included to show that the matrix band can also be translucent or transparent in contrast to the opaque matrix bands which are typically formed from stainless steel. Matrix bands which are at least translucent or which have portions which are at least translucent enable a practioner to direct light through the matrix band to harden a light polymerizable filling material. Not only can light pass through the band but the light tends to diffract or scatter, particularly when the light passes through a frictional engagement surface. The uneven roughened texture of frictional engagement surfaces which are translucent or transparent causes the scattering effect. Any material which is utilized for translucent or transparent matrix bands may be utilized within the scope of the present invention to yield matrix bands which are at least translucent and which have a frictional engagement surface on their exterior sides. Such bands may be integrally formed from a single material such as polyester or Mylar™ sold by DuPont. FIG. 6K depicts a matrix band 100k which has a smooth stainless steel half 108k and the other half 109k is formed from a plastic which is clear or at least translucent with a portion of the exterior side of the plastic half being a frictional engagement surface.

Note that the dental matrix bands are preferably configured such that conformance of the dental matrix band around a tooth requiring restoration renders the dental matrix band unsuitable for any subsequent use. More particularly, once adapted to a patient's tooth the dental matrix band cannot then be used on another patient due to the structure of the matrix band or due to the physical properties of the material from which the matrix band is formed. For example, the type of metal used and the thickness of the dental matrix band preferably is selected such that the resilience of the matrix band reduces the ability of the matrix band to be readapted. This prevents the matrix band from being used in a potentially unsanitary manner. For the same purpose, the dental matrix is preferably preloaded in a dental matrix band holder which prevents the matrix band from being removed in a reusable manner such as those discussed hereinbelow in relation to FIGS. 7–15. The configuration of the matrix bands, particularly the curvature of matrix bands such as are shown in FIGS. 6A–6L, also prevents the matrix band from being subsequently used for other purposes such as the matrix bands used as sanding strips which are disclosed in U.S. Pat. No. 4,563,152.

Figure 6M:
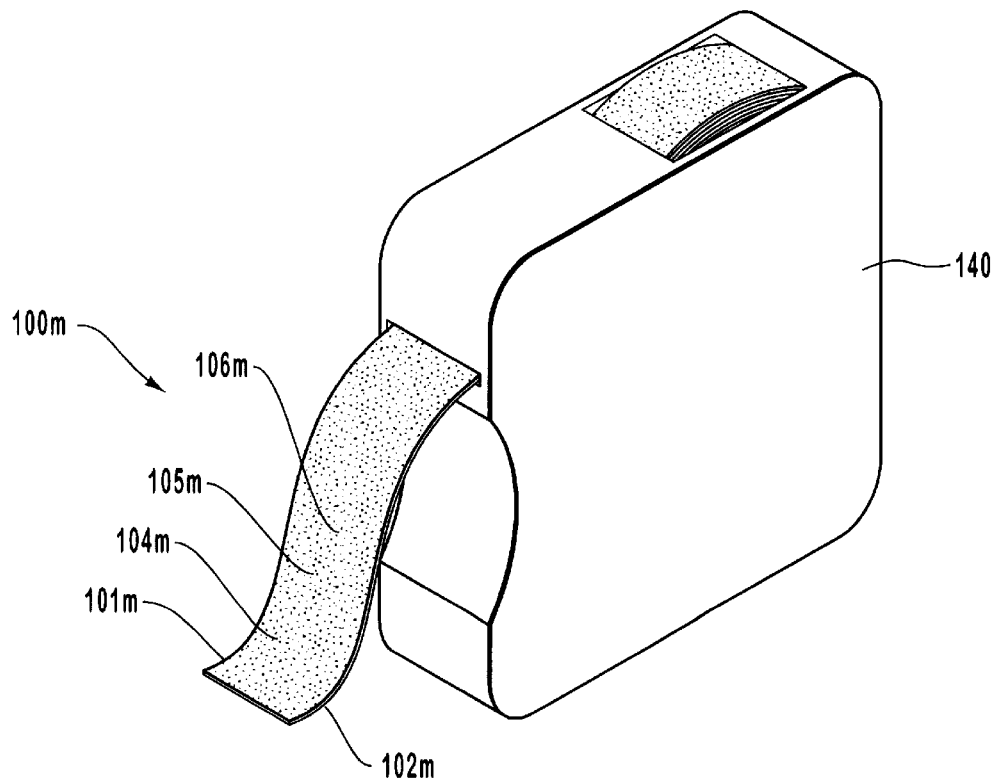

The matrix bands may be sold as shown in FIGS. 6A–6L in bulk quantities or on a spool as shown in FIG. 6M for the dentist to load into a conventional matrix band holder such as those known as Tofflemire band holders. An example of such Tofflemire band holders is disclosed in U.S. Pat. No. 2,502,903. The matrix band can also be used with other band holders such as those disclosed in U.S. Pat. No. 2,686,970 issued to Reiter; U.S. Pat. No. 2,687,573 issued to Stone; U.S. Pat. No. 2,709,302 issued to Reiter; U.S. Pat. No. 2,722,746 issued to Brenner; U.S. Pat. No. 3,425,125 issued to Bergendal; U.S. Pat. No. 3,516,162 issued to Ainsworth; U.S. Pat. No. 3,908,273 issued to Reiter; U.S. Pat. No. 4,824,365 issued to von Weissenfluh; U.S. Pat. No. 4,915,627 issued to Hirdes; U.S. Pat. No. 5,626,475 issued to von Weissenfluh and German Patent Document No. 2,603,130 A1. Each of these patent references is hereby incorporated by specific reference. Each band holder disclosed in these references is an example of means for positioning a matrix band around a tooth to enable the matrix band to be used in filling a dental preparation.

The matrix bands are more preferably preloaded into a dental matrix band holder or retainer clamp such as the clamps sold by Ultradent Products, Inc. of South Jordan, Utah as Omni™ matrix band clamps. Examples of Omni™ matrix band clamps are disclosed in U.S. Pat. No. 5,342,197 which issued to Stein et al. and U.S. Pat. No. 5,055,045 which issued to Dickie. Both of these patents are hereby incorporated by specific reference. The band holders disclosed in these two patents are additional examples of means for positioning a matrix band around a tooth to enable the matrix band to be used in filling a dental preparation.

FIGS. 7A–7D provides an example of a matrix band at 200 used with a dental matrix band holder shown at 210. Dental matrix band holder 210 has a main body element 230 with a head element 240 pivotally mounted thereon at the tooth engagement end 212. More detailed views of head element 240 are shown in FIGS. 8A–D. FIGS. 9A–9C depict the interaction between dental matrix band holder 210 and head element 240. These band holders, as well as all other band holders disclosed herein including those disclosed in U.S. patent application Ser. No. 09/356,629 which was previously incorporated, provide further examples of means for positioning a matrix band around a tooth to enable the matrix band to be used in filling a dental preparation. The holders disclosed herein are also, more specifically, examples of means for positioning a matrix band around a tooth and then holding the matrix band to enable the matrix band to be used in filling a dental preparation.

As shown best in FIG. 7A, main body element 230 has a generally centrally located first longitudinal axis 215, and a first opposed lateral side 232a and a second opposed lateral side 232b. A pair of opposed flange members 234a and 234b (viewable in FIGS. 7C–D) extend outwardly from main body element 230 in a spaced apart generally parallel planar relation one to the other, and are thereby adapted to receive and retain head element 240 in operative relation therebetween, as will be discussed in greater detail. Head element 240 is one example of a head means for pivoting the binding means. The head elements disclosed herein are preferably translucent.

Matrix band 200 may be a metal matrix band, a translucent matrix band or a combination thereof. All of the dental matrix bands disclosed herein are examples of binding means for positioning around a tooth requiring restoration in order to contain a restorative dental composition.

Figure 7B:
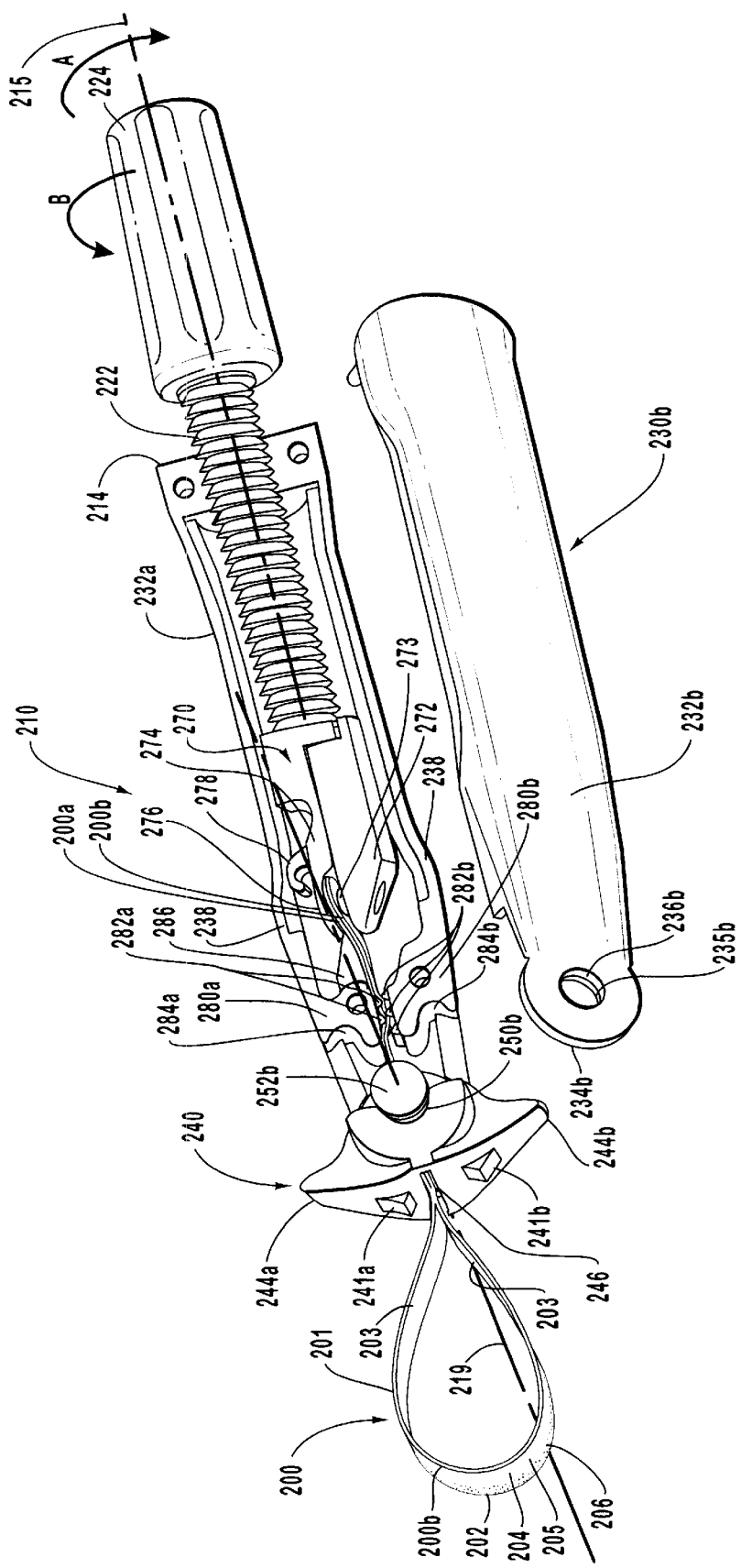
FIG. 7B is a perspective view of the dental matrix retainer clamp shown in FIG. 7A with lateral side 230b of main body element 230 removed.

Matrix band 200 is shown being elongated and forming a loop extending outwardly from head element 240 through a generally centrally located guide slot 246. As shown in FIG. 7B, matrix band 200 has two opposite ends identified as first end 200a and second end 200c with a midsection 200b therebetween. Matrix band 200, more particularly, midsection 200b of matrix band 200, has a slightly curved configuration such that midsection 200b is scooped to enable the matrix band to anatomically conform to a tooth when positioned around the tooth. In other words, the loop or midsection 200b of matrix band 200 is slightly smaller in perimeter at bottom edge 202 than in its perimeter at its top edge 201 as seen in FIGS. 7A–D. Matrix band 200 is typically engaged on a tooth with bottom edge 202 toward the gingiva and top edge 201 toward the top of the tooth.

Interior side 203 of matrix band 200 is shown having a smooth surface to be engaged against a tooth requiring restoration. Exterior side 204 of matrix band 200 is shown having a surface 205 which is at least partially a frictional engagement surface 206 adapted to provide frictional engagement with a dental wedge. More particularly, frictional engagement surface 206 of the exterior side 204 of dental matrix band 200 extends from bottom edge 202 upward toward top edge 201 at least one-third of the distance between bottom edge 202 and top edge 201.

The two ends 200a and 200c of matrix band 200 are operatively retained within main body element 230 on an adjustment mechanism. The adjustment mechanism includes at least a threaded rod 222 and a block 270 mounted as a swivel upon threaded rod 222. As can be seen in FIG. 7B, the ends 200a and 200c of matrix band 200 are secured to block 270. Thereby, turning of threaded rod 222 makes the loop size of matrix band 200 adjustable.

Threaded rod 222 is threadably engaged by main body element 230, and extends outwardly from the adjustment end 214 of main body element 230. A gripping member 224 is located on threaded rod 222, near adjustment end 214, so as to permit threaded rod 222 to be readily turned with respect to main body element 230. When gripping member 224 is turned in a first direction, as indicated by arrow "A", matrix band 200 is extended so as to increase the size of the loop that it forms. When gripping member 224 is rotated in a second direction, opposed to first direction "A", as indicated by arrow "B", matrix band 200 is retracted, thereby decreasing the size of the loop, so as to tighten matrix band 200 securely around a tooth.

During movement of matrix band 200, matrix band 200 moves between tensioning guides 282a and 282b which are small ridges integrally located on the surfaces of opposing extensions 280a and 280b. Movement of matrix band 200 across tensioning guides 282a and 282b helps to ensure that the size of the portion of matrix band extending from head element 240 is smoothly adjusted. Tensioning guides 282a and 282b also help prevent the matrix band from moving once properly adjusted as they prevent slippage.

Extensions 280a has an integral member, wedge 286, extending toward block 270. Wedge 286 splits block 270 into two parts, a retention pin block 272 and a spring block 274, when block 270 is advanced into wedge 286. As discussed below, when wedge 286 splits block 270, the ends of matrix band 200 are released from their position relative to block 270. This occurs after completing a dental procedure when the size of the loop is greatly increased to remove the clamp from a tooth. By releasing the ends of matrix band 200, further adjustment of matrix band 200 is not possible, thereby limiting the dental matrix band holder 210 to a single use to ensure safety standards. Wedge 286 is one example of means for releasing the matrix band 200. Stated otherwise, wedge 286 is an example of means for releasing the binding means from the block.

The ends of matrix band 200 have holes in them which are positioned around a retention pin 273. Retention pin 273 is an integral portion of the retention pin block 272 which is shown having a semicircular or rounded shape with a diameter that is smaller than that of the holes in the ends of matrix band 200. Retention pin 273 of retention pin block 272 is shown in contact with a retention flange 276 of spring block 274 to enable matrix band 200 to be moved as block 270 is moved. Spring block 274 also has a block spring 282 extending therefrom which helps ensure that retention flange 276 stays in contact with retention pin 274 until wedge 286 pushes retention flange 276 upward. More particularly, block spring 282 pushes against the interior of wall 274 of main body element 230, thereby enabling retention flange 276 to push against retention pin 273 to hold the ends of matrix band together in a stationary position relative to block 270. Note that both retention flange 276 and block spring 282 are both integral portions of spring block 274.

The adjustment mechanism described above as including at least threaded rod 222 and block 270 is an example of an adjustment means for moving the binding means. Block 270 is an example of means for coupling matrix band 200 with threaded rod 222. Another example of such a coupling means is a block which is a single element which has a hook for insertion through the ends of matrix band 200. Retention pin 273 of retention pin block 272 and retention flange 276 of spring block 274 are an example of attachment means for attaching a matrix band to a block. A hook extending from a solid block is also an example of a attachment means.

It should be noted that the dental matrix band holder 210 is symmetrical from side to side about first longitudinal axis 215 when seen in plan view, and is symmetrical from top to bottom about first longitudinal axis 215 when seen in elevational side view. Accordingly, head element 240 in its first locked position is completely equivalent to head element 240 in its second locked position. The advantage of being able to lock head element 240 in either one of first and second positions is that dental matrix band holder 210 can be used on teeth on either side of a patient's mouth in an equivalent manner. Head element 240 is typically in its first locked position when in place on a patient's tooth in the upper right or lower left quadrant of the mouth, as discussed in greater detail below in reference to FIG. 9A. Similarly, head element 240 is typically in its second locked position when in place on a patient's tooth in the upper left quadrant or the lower right quadrant of the mouth, as discussed in greater detail below in reference to FIG. 9C.

Figure 3:
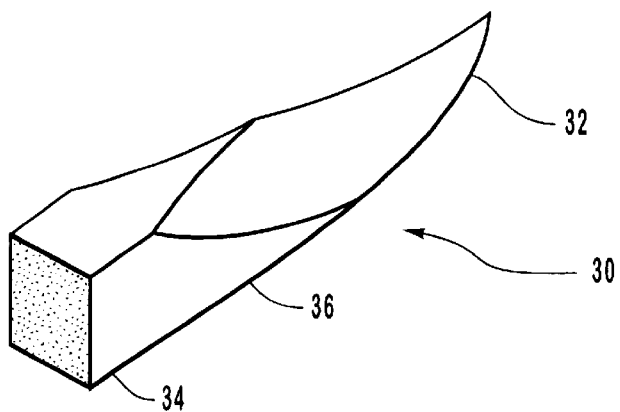
FIG. 3 is a view of a dental wedge of the prior art.
Figure 7C:
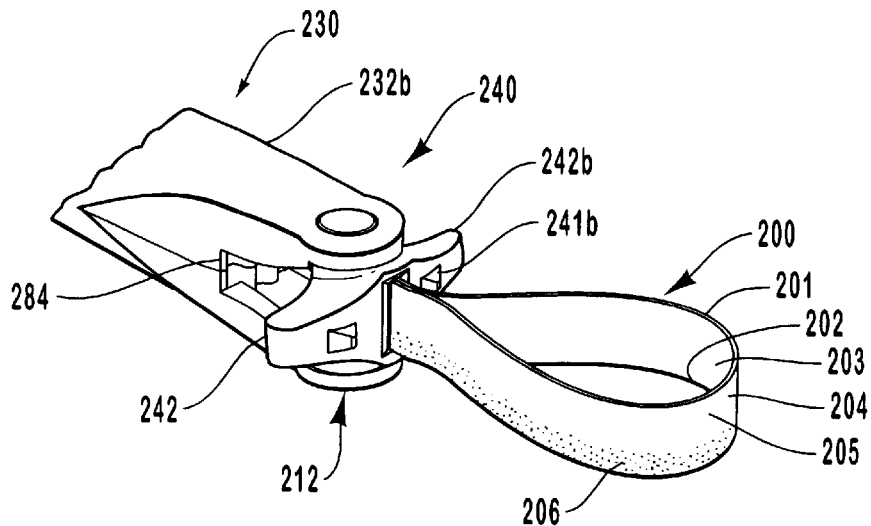
FIG. 7C is a partial perspective view of the tooth engagement end of the dental matrix retainer clamp shown in FIGS. 7A–7B.
Figure 7D:
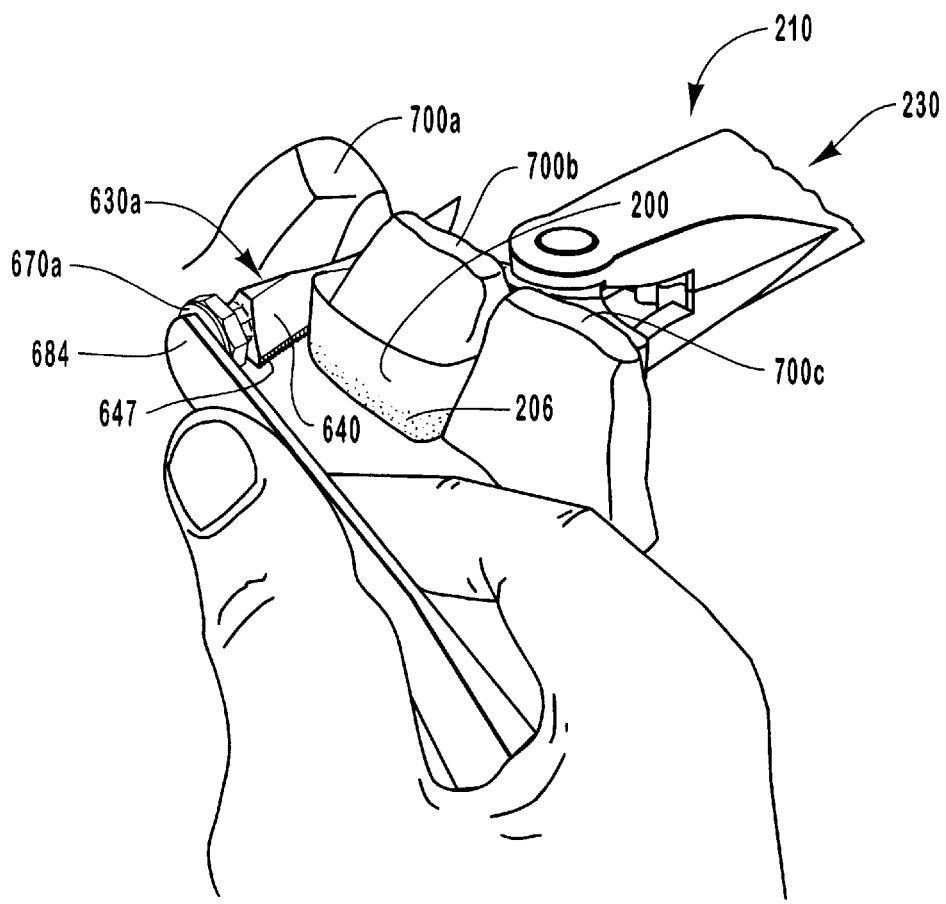
FIG. 7D is an partial perspective view of the tooth engagement end of the dental matrix retainer clamp shown in FIGS. 7A–7C holding a matrix band around a tooth and a dental wedge holding the matrix band in position.
Figure 8A:
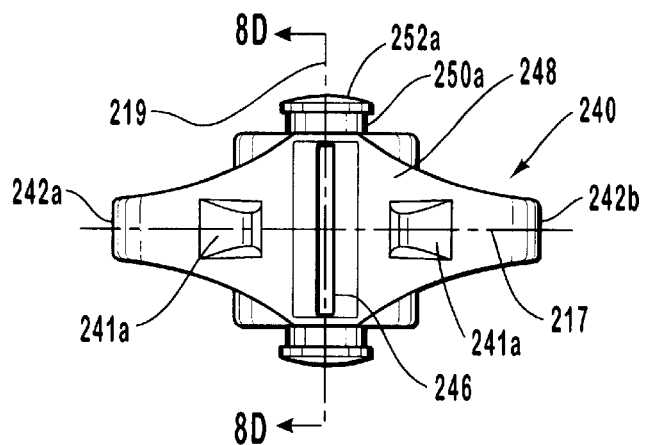
FIG. 8A is a front end view of the head element of the dental matrix retainer clamp of FIGS. 7A–7D.
Figure 8B:
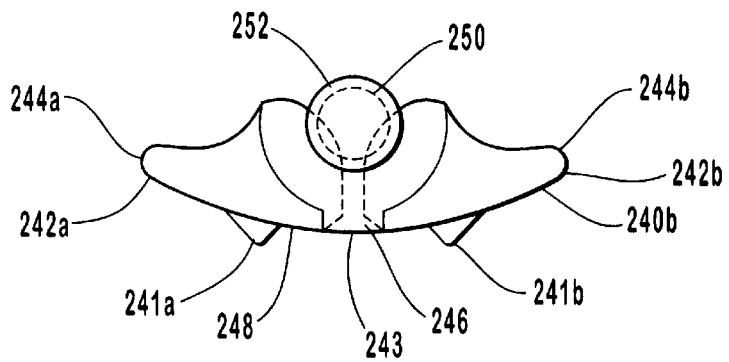
FIG. 8B is a side view of the head element of FIG. 8A.
Figures 8C, 8D:
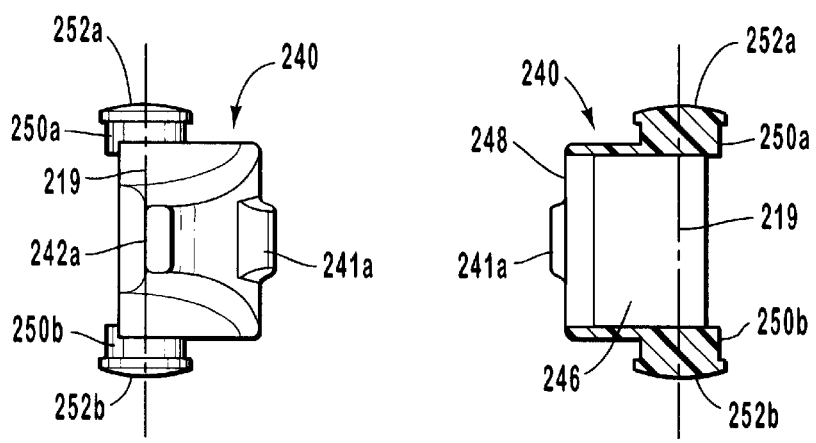
FIG. 8C is an end view of the head element of FIG. 8A.
FIG. 8D is a cross-sectional view of the head element of FIG. 8A, taken along section line 8D—8D.

As seen generally in FIG. 7C, and in FIGS. 8A–D with greater detail, head element 240 has a first end 242a, a second end 242b and a generally centrally located second longitudinal axis 217 that extends from first end 242a to second end 242b. As seen in FIG. 3, head element 240 is divided into two symmetrical halves at second longitudinal axis 217, and is thereby longitudinally symmetrical. An anterior surface 248 is adapted to interface with the outer facing portion of a tooth by way of a pair of opposed supporting shoulders 241a and 241b, one supporting shoulder on each of the symmetrical halves of head element 240. Between the pair of opposed supporting shoulders 241a and 241b is a recessed area 243 that has guide slot 246 centrally located therein, as seen in FIG. 3. Head element 240 is pivotally mounted on the tooth engagement end 212 of matrix band holder 210 for angularly variable movement about a pivot axis 219 that is perpendicular to first longitudinal axis 215 and located midway between first opposed lateral side 232a and second opposed lateral side 232b.

Opposed supporting shoulders 241a and 241b may be located on head element 240. They are located on anterior surface 248 and are shaped and dimensioned to be in supporting contact with matrix band 200 when matrix band 200 is snugly in place around a tooth, on an as-needed basis, depending on the shape and size of the tooth being worked on. As will be discussed further below, the shape of head element 240 and of opposed supporting shoulders 41 as well as the translucence of head element 240, facilitates visibility for the dental professional and also facilitates useful transmission and/or redirection of a curing light beam during specific dental procedures. Opposed supporting shoulders 241a and 241b prevent the loop of matrix band 200 that is in place around a tooth from moving laterally with respect to head element 240, thereby allowing matrix band 200 to be kept in proper placement around the tooth.

As indicated herein above, head element 240 is preferably made of a material that is translucent. Examples of translucent materials include synthetic plastics, organic translucent resins, strands of fiber optic material, glass, and the like. Alternatively, main body element 230 as well as all other parts may also be made of a translucent material. Included therein is matrix band 200 as being optionally made of a translucent material. Examples of translucent materials for matrix band include synthetic plastics, organic translucent resins, and the like. Polyester films, such as Mylar™, are particularly useful.

The pivoting capability of head element 240, seen in FIGS. 7A and 9A–9C, and as used in the present invention, is demonstrated by a pair of oppositely directed mounting posts 250a and 250b that are provided and that are received in co-operating apertures 235a and 235b located one each on respective sides of opposed flange members 234a and 234b. In this manner, head element 240 is pivotally mounted with respect to main body element 230 between its first locked position, as shown in FIG. 9A, at which head element 240 is disposed toward first lateral side 232a of main body element 230 and its second locked position, as shown in FIG. 9C, at which head element 240 is disposed toward second lateral side 232b of main body element 230. The first and second locked positions correspond to the intermediate positions of dental matrix band holder 210 in a person's mouth, at which main body element 230 is disposed to one side of the tooth being worked on. As seen in FIG. 9B, there is also an intermediate position between the first and second locked positions such that first longitudinal axis 215 symmetrically bisects holder or clamp 210. Thus, when head element 240 has a neutral orientation, the orientation of second longitudinal axis 217 also symmetrically bisects holder 200 in a direction that is perpendicular to first longitudinal axis 215.

In order to lock head element 240 in its first locked position, there is a first locking mechanism in the form of a first detent portion 284a on the main body element 230, or more particularly on extension 280a. First detent portion 284a interacts with a co-operating first protruding portion 244a at first end 242a of head element 240. In this locked position, the dental professional's line of sight is generally directed along the side of dental matrix band holder 210, but a portion of the line of sight may be obscured by second end 242b of head element 240. According to the present invention, the dental professional's line of sight is less obscured or not obscured at all due to the translucent material that head element 240 is made of. Additionally, where light is being directed onto a tooth that is restrained within matrix band 200, the path of the curing light, L, is substantially less obscured by second end 242b of head element 240 because of its translucent nature.

Similarly, in order to lock head element 240 in its second locked position, a second locking mechanism in the form of a second detent portion 284b on main body element 230, or more particularly on extension 280b, interacts with a co-operating second protruding portion 244b at second end 242b of head element 240. First detent portion 284a retains first end 242a of head element 240 in an interference fit therewith when head element 240 is in its first locked position. Similarly, second detent portion 284b retains the second end 242b of head element 240 in an interference fit therewith when head element 240 is its second locked position. In order for this interference fit type of locking mechanism to work properly head element 240 will deform slightly in order to permit first and second protruding portions 244a, 244b to move past the respective of first and second detent portions 284a, 284b.

In order to properly accommodate the interference fit type locking mechanism of the first locking mechanism and the second locking mechanism, head element 240 is somewhat loosely retained by main body element 230. More particularly, mounting posts 250a and 250b are engaged in loosely held relation in co-operating apertures 235a and 235b so as to allow a small amount of lateral movement of mounting posts 250a and 250b with respect to main body element 230. Such lateral movement of mounting posts 250a and 250b allows the interference fit between first end 242a and second end 242b of head element 240 and the respective of first and second detent portions 284a, 284b to be accommodated. This means that, in practice, the diameter of each of mounting posts 250a and 250b is approximately 0.15 mm less than the diameter of respective co-operating apertures 235a and 235b. This approximate 0.15 mm difference in dimensions provides for a slightly larger clearance than a difference of about 0.05 mm, which would normally be the difference in dimensions that is typically found in a conventional interference fit configuration of two small plastic pieces. If a conventional clearance of about 0.05 mm were to be provided between mounting posts 250a and 250b and co-operating apertures 235a and 235b, the passing of first and second protruding portions 244a, 244b over respective first and second detent portions 284a, 284b would be accommodated mostly by the deformation of head element 240 and accommodated to a small degree by the 0.05 mm clearance. In that event, an undue force must be applied to head element 240 in order to move head element 240 into or out of either of its first or second locked positions. However, because of the small size of head element 240, the moment arm between first end 242a and second end 242b of head element 240 and its pivot point are each quite small. Thus, a somewhat large force—usually applied at one of first end 242a and second end 242b—would be required to manipulate head element 240 into its first and second locked positions. Therefore, it would be difficult to snap head element 240 into its first and second locked positions if a clearance of about 0.05 mm were used in conjunction with a conventional interference-fit type locking mechanism.

In the present invention, therefore, in order for the locking and the unlocking of head element 240 to be relatively easily performed, it is preferable that only a relatively small operating force by the fingers be required. To functionally minimize such forces, the interference fit between either of first end 242a and second end 242b of head element 240 with the respective of first and second detent portions 284a, 284b may be functionally minimized. At the same time, first end 242a and second end 242b may be sufficiently blocked, respectively by, first and second detent portions 284a, 284b so as to hold head element 240 in the respective of its first and second locked configurations. These seemingly contradictory requirements can be met by the slightly larger-than-conventional clearance between mounting posts 250 and co-operating apertures 235 of about 0.15 mm. This particular clearance can allow head element 240 to move laterally during locking and unlocking, so that the physical displacement of the material of head element 240 that is useful to allow first end 242a and second end 242b to move past respective first and second detent portions 284a, 284b can be reduced to an optimum level.

It is therefore desirable to use a slightly larger-than-conventional clearance between mounting posts 250a and 250b and co-operating apertures 235a and 235b so that the deformation of head element 240 can be reduced during locking and unlocking of head element 240. In this manner, manipulation of head element 240 into and out of either of the first and second locking positions is possible, by way of relatively low-force thumb and finger operation.

Mounting posts 250a and 250b each have an enlarged head portion thereon respectively identified at 252a and 252b. Correspondingly, co-operating apertures 235a and 235b each have an enlarged end portion respectively identified at 236a and 236b which is configured to act as a rim or flange. More particularly, each enlarged end portion 236 is adapted to receive the respective large head portion 252 therein, so that they thereby securely retain head element 240 within opposed flange members 234a and 234b. The diameter of each enlarged head portion 252 of each mounting post 250 is preferably at least 0.15 mm less than the respective cooperating enlarged end portion 236 of each co-operating aperture 235, but is also preferably about 0.15 mm larger than the diameter of the co-operating aperture 235. This slightly larger dimension of enlarged end portions 236a and 236b can permit head element 240 to be relatively securely retained between flange members 234a and 234b.

When the disposable dental matrix band holder is to be used, a decision can first be made to move main body element 230 out of the way of the tooth, at least as much as possible so that the tooth may be worked on. Thus, main body element 230 can be pivoted to one side or the other and may then be locked in place in either of the first or second locked positions, as appropriate, so as to remain out of the way. Then, an adjustment can be made so that the size of the loop formed by matrix band 200 is at least large enough to fit over the tooth. Matrix band 200 can then be placed in the mouth around the tooth, and gripping member 224 can be turned in the second direction, as indicated by arrow "B", so as to pull the end of matrix band 200 into main body element 230 and to thereby tighten matrix band 200 onto the receiving tooth. The dental procedure then continues.

The most prominent feature of head element 240 as seen in FIGS. 9A–9C is the radius, $r_3$, taken from the center of enlarged head portion 252a and running radially therefrom to opposed supporting shoulder 241a. Reference to FIG. 9C illustrates a first radius, $r_1$, that constitutes a line taken from the center of enlarged head portion 252a and running radially therefrom to the perimeter of opposed flange member 234a and 234b. Third radius, $r_3$, is taken from the center point of enlarged head portion 252a and runs radially therefrom to either first end 242a or second end 242b of head element 240. The ratio of $r_3$ to $r_1$ in the embodiment shown in FIG. 9 may be taken to be about 3:1 or larger.

The pivoting capability of head element 240 as discussed above, may be applied to selected embodiments set forth below. The locking capability of head element 240 as discussed above, may be applied to the proceeding embodiment of a head element 340.

As can be seen in FIGS. 10A–10E, another embodiment of the present invention comprises a head element 340 having prominences 358a and 358b in place of opposed supporting shoulders 241a and 241b, seen in FIGS. 7A–7D, 8A–8D and 9A–9C. Prominences 358 have substantially the same elevation as opposed supporting shoulders 241a and 241b of head element 240. However, anterior surfaces 348a and 348b are curved so as to have substantially smooth curvilinear configurations that are not possible where opposed supporting shoulders 241a and 241b are present.

Figure 10A:
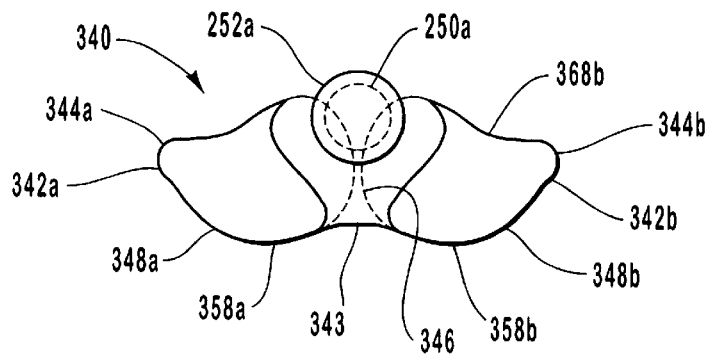
FIG. 10A is a top view of a head element of an alternative embodiment of the present invention.

Like head element 240, head element 340 is also preferably substantially translucent. Because anterior surfaces 348a and 348b, as seen also in FIGS. 10A–10E, have a substantially smooth curvilinear configuration, it is easier for the dental professional to look through head element 340. As seen in FIGS. 10A and 10E, a posterior surface 368b of head element 340 has a substantially smooth curvilinear configuration as does anterior surface 348b. It can be seen that posterior surface 368b may be concave and anterior surface 348b may be convex. Because opposed supporting shoulders 241a and 241b of head element 240 have nonsmooth angles, they tend to make visibility through them more difficult than through prominences 358 of this embodiment.

Figure 10B:
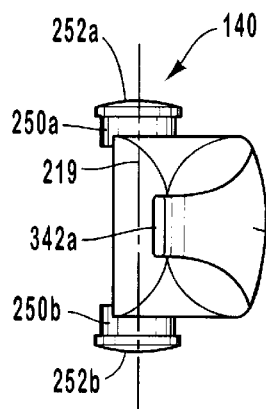
FIG. 10B is an end view of the head element of FIG. 10A.

The side view presented in FIG. 10B makes it apparent that since head element 340 has prominences 358a and 358b in place of opposed supporting shoulders 241a and 241b, prominences 358a and 358b represent the prominent features thereof at a length relative to the center of rotation substantially equal to the distance extending radially from the center of mounting post 250a of opposed supporting shoulders 241a and 241b as seen in FIGS. 7A–7D, 8A–8D and 9A–9C. Prominences 358 are configured for engagement against tooth surfaces. More particularly, prominences 358 rest substantially against matrix band 200 or against a tooth during use when head element 340 is pivoted or fixed.

Figure 10C:
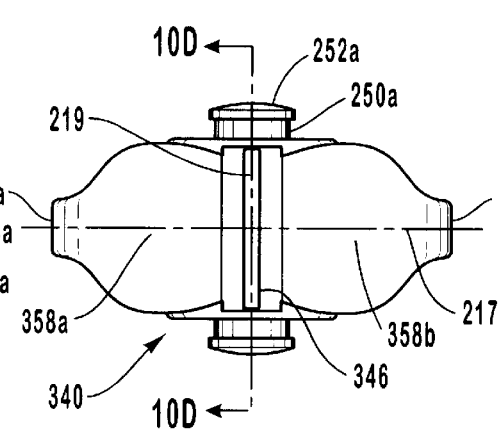
FIG. 10C is a front end view of the head element of FIGS. 10A–B.
Figure 10D:
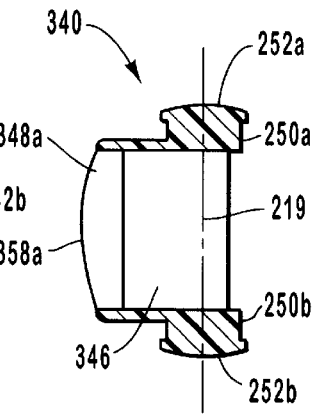
FIG. 10D is a cross-sectional view of the head element of FIGS. 10A–C, taken along section line 10D—10D.
Figure 10E:
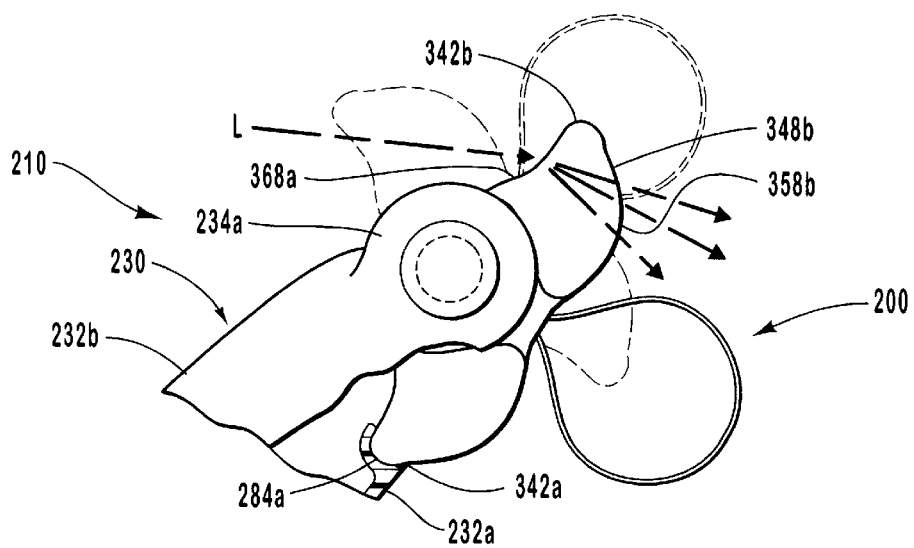
FIG. 10E is a top plan view of the dental matrix retainer clamp with the head element of FIG. 10A in a first locked position and depicting the transmission of light through one end of the head element.

FIG. 10C provides a front view of head element 340. From this view, it can be seen that prominence 358a is substantially the center between first end 242a of head element 340 and guide slot 246. Similarly, prominence 358b is substantially the center between second end 242b of head element 340 and guide slot 246. FIG. 10D is a cross section of head element 340 taken along the line 10D–10D. It can be seen that prominence 358 represents the most prominent point of head element 340 upon anterior surface 248. The other elements of head element 340 are essentially the same as that of head element 240. More particuarly, head element 340 has ends 342a and 342b, recessed area 343, protruding portions 344a and 344b, and a guide slot 346 which correspond with the similarly identified elements of head element 240.

FIG. 10E illustrates employment of the inventive dental matrix band holder 210 as light, L, is being directed thereto. It can be seen that light L strikes head element 340 at posterior surface 368b and instead of casting a shadow upon matrix band 200 and/or adjacent teeth, light is transmitted therethrough. Additionally, where head element 340 is structured to have prominences 358a and 358b, light is more uniformly dispersed therethrough as in comparison to head element 240 of FIGS. 7A–7D, 8A–8D and 9A–9C embodying opposed supporting shoulders 241a and 241b. Depending upon the particular application, the use of head element 240 having opposed supporting shoulders 241a and 241b or head element 340 having prominences 358 may be selected.

Figure 12A:
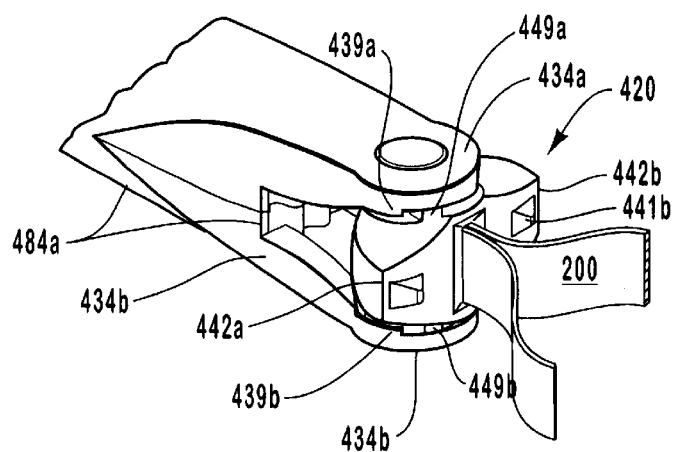
FIG. 12A is a perspective view of another embodiment with a reduced dimension.

In another embodiment of the present invention, a head element 440, as illustrated in perspective view in FIGS. 12A–D and 14, has two modifications over head elements 240, 340, seen above. Head element 440, as seen in FIG. 12A, has a significantly reduced length between a first end 442a and a second end 442b. Thus a reduced profile is accomplished that makes it easier for the dental professional to see and/or for the transmission of light onto the patients tooth. In order to accomplish this reduced profile, the detent portions are located upon head element 440 instead of on main body element 430. This signifies that the protruding portions that lock into the detent portions are located upon opposed flange members 434a and 434b of main body element 230 instead of on head element 440.

Like head elements 240 and 340, head element 440 also has a recessed area 443, a guide slot 446, anterior surfaces 448a and 448b, mounting posts 450a and 450b, enlarged head portions 452a and 452b which correspond with the similarly identified elements of head elements 240 and 340. Head element 440 is shown having shoulders 441a and 441b like head element 240; however, head element 440 can also have prominences such as prominences 358 of head element 340 instead of shoulders.

Figure 12B:
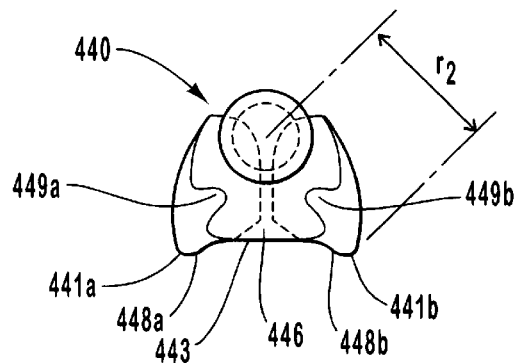
FIG. 12B is a top view of the head element of the embodiment shown in FIG. 12A.
Figure 12C:
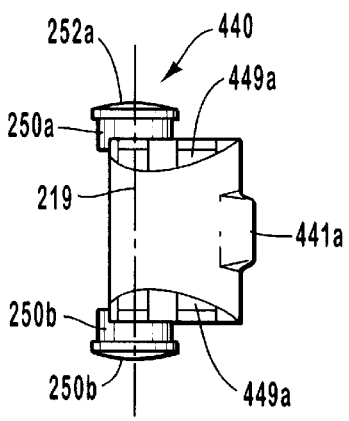
FIG. 12C is an end view of the head element of FIGS. 12A–B.
Figure 12D:
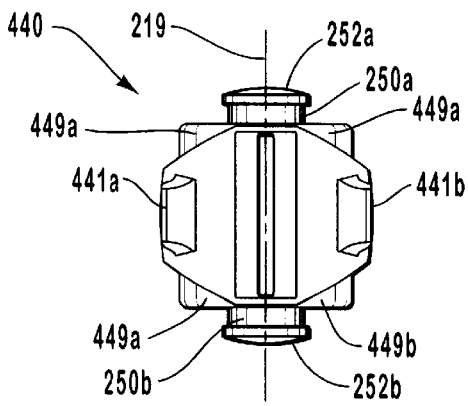
FIG. 12D is a front-end view of the head element of the dental matrix retainer clamp of FIGS. 12A–C.

FIG. 12B is an elevational front side view of head element 440. As seen in FIGS. 12B–12D, head element detent portions 449a and 449b are located upon head element 440. Head element detent portions 449a and 449b have a concave contour. Head element 440 will, upon sufficient rotation thereof, engage a protruding portion on either opposed flange member 434a or 434b.

Similarly to what is taught above as an interference fit for other embodiments, head element detent portions 449a and 449b respectively lock main body element flange protruding portions 439a and 439b (see FIG. 14) in an interference fit. Similarly as taught above, all dimensional tolerances that are useful for both locking and unlocking of head elements 240, 340, with main body element 230 are employed in this embodiment for locking head element 440 with main body element 430. In particular, all dimensional tolerances taught above are incorporated in locking head element detent portions 449a and 449b and into main body element flange protruding portions 439a and 439b.

Additionally, main body element 430 is configured like main body element 230 with only a few exceptions. As indicated above, head element 440 has main body flange protruding portions 439a and 439b instead of detent portions 284a and 284b. Accordingly, the interior walls 438a and 438b as well as the opposing extensions 480a and 480b may also be configured differently from the corresponding elements of head element 240 as shown.

The most prominent feature of head element 440 as seen in FIG. 12B is at the radius, $r_2$, taken from the center of enlarged head portion 252a and running radially therefrom to opposed supporting shoulder 441b. Reference to FIG. 9C illustrates a first radius, $r_1$, that constitutes a line taken from the center of enlarged head portion 252a and running radially therefrom to the perimeter of opposed flange member 234a. The ratio of $r_2$ to $r_1$ in the embodiment shown in FIG. 12B may be taken to be about 2:1. Where opposed supporting shoulders 441a and 441b may have a height less than $r_2$ depicted in FIG. 12B, or where opposed supporting shoulders may not be required, the ratio of $r_2$ to $r_1$ may be about 1.5:1, more preferably about 1.25:1 and most preferably about 1:1. Thereby, the profile of head element 440 may be substantially reduced under any of the above preferred ratios to facilitate the dental professional's visibility to the patient's tooth.

FIG. 12C is a side view of head element 440 depicted in FIG. 12B. Therein, it can be seen that head element detent portions 449 are configured to engage main body element flange protruding portions 439, seen in FIG. 14, upon sufficient rotation thereof.

FIG. 12D illustrates a front-end view of head element 440 for this embodiment, wherein it can be seen that opposed supporting shoulders 441a and 441b represent the extreme outer dimensions thereof. Head element detent portions 449 are represented as hidden from this view.

FIGS. 13 and 14 illustrate main body element 230 and main body element 430,respectively, that have been taken apart to reveal the interiors thereof and the differences between them. Therein it can be seen that main body element flange protruding portions 439 are extensions of the wall 438 of main body element 430. As such, they are part of opposed flange member 434b. As head element 440 is inserted by enlarged head portion 252a into cooperating aperture 435b, and rotated sufficiently, main body element flange protruding portions 439a and 439b are respectively inserted and locked into head element detent portions 449a and 449b. The combination of embodiments is also useful by having detent portions located both on the head element and on the main body element as set forth above. Additionally, a full-length head element as seen in FIGS. 7A–D, may be combined with a detent portion as seen in FIGS. 12A–12D and 14.

Figure 15A:
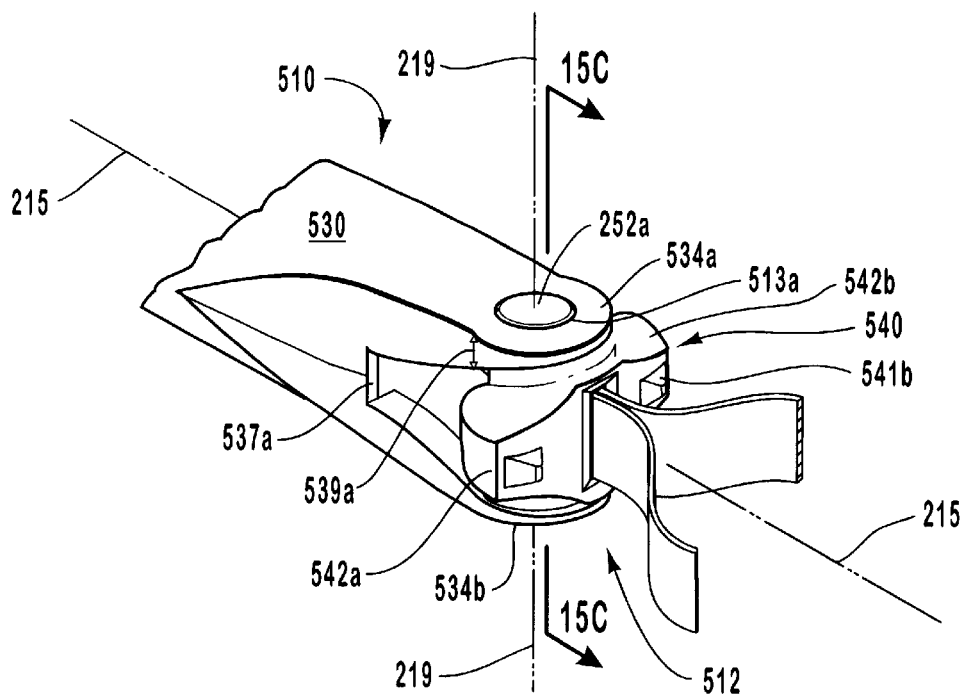
FIG. 15A is a perspective view of an alternative embodiment of the inventive dental matrix retainer clamp, wherein a wedge shaped head element is rotated to experience friction that increases proportional to the degree of rotation.

FIG. 15A is a perspective view of an alternative embodiment of the present invention. While the flanges members define an opening in all of the embodiments disclosed herein, the opposed flange members 534a and 534b of main body element 530 define an opening which is tapered to decrease in size from a front pivot portion 513 of main body element 530 to stop portions 539a and 539b on each side of the main body element 530. Each stop portion 539 terminates at a stop end 537. In this embodiment, no coupled detent mechanism is necessary as in the other embodiments, although it may be useful in some instances to also have both.

Head element 540 has ends 542 which are wedge shaped. The wedge shape corresponds with that of stop portions 539 of the opening defined by flange members 534a and 534b of main body element 530. The complementary shapes and the position of ends 542a and 542b enable head element 540 to pivot freely until an end 542 of head element 540 is pushed against one of the stop portions to frictionally lock one of the ends 542 of head element 540 against one of the stop portions. Stated otherwise, because opposed flange members 534 increase in thickness from front pivot portion 513 toward stop ends 537, the wedge shape of head element 540 causes friction to increase during rotation to a first side or to a second side from a neutral position as shown in FIG. 15A. The ability of head element 540 to be moved with increasing friction enables it to be placed in various positions depending on the amount of friction desired or the degree to which the position must be secured.

Figure 15B:
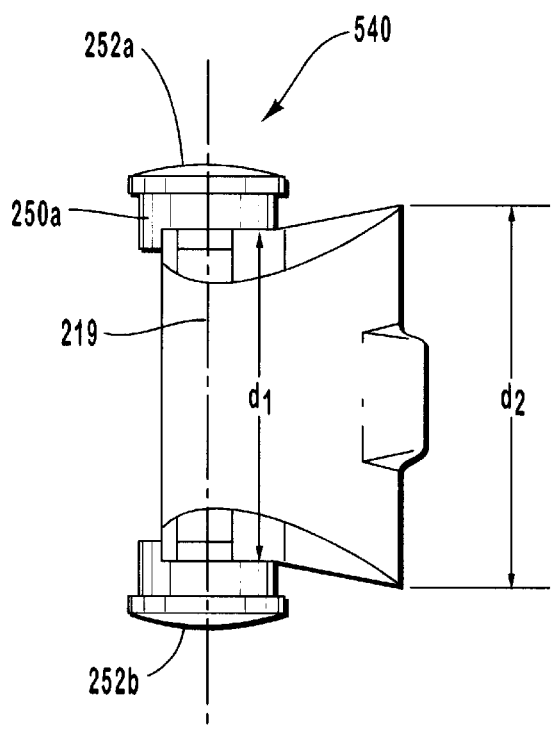
FIG. 15B is an elevational side view of the head element depicted in FIG. 15A, wherein the wedge shape of the head element is illustrated to depict increasing friction that is applied against the opposed flange members.

FIG. 15B is an elevational side view of head element 540 in which the wedge shape thereof is further illustrated. It can be seen that a first dimension $d_1$ defines the smaller dimension of the wedge shape of head element 540 and that a second dimension $d_2$ defines the larger dimension of the wedge shape of head element 540. As head element is rotated about pivot axis 219, opposed flange members 534a and 534b offer increasing frictional resistance to rotation due to their tapered shape that is opposite to the shape of head element 540.

Figure 15C:
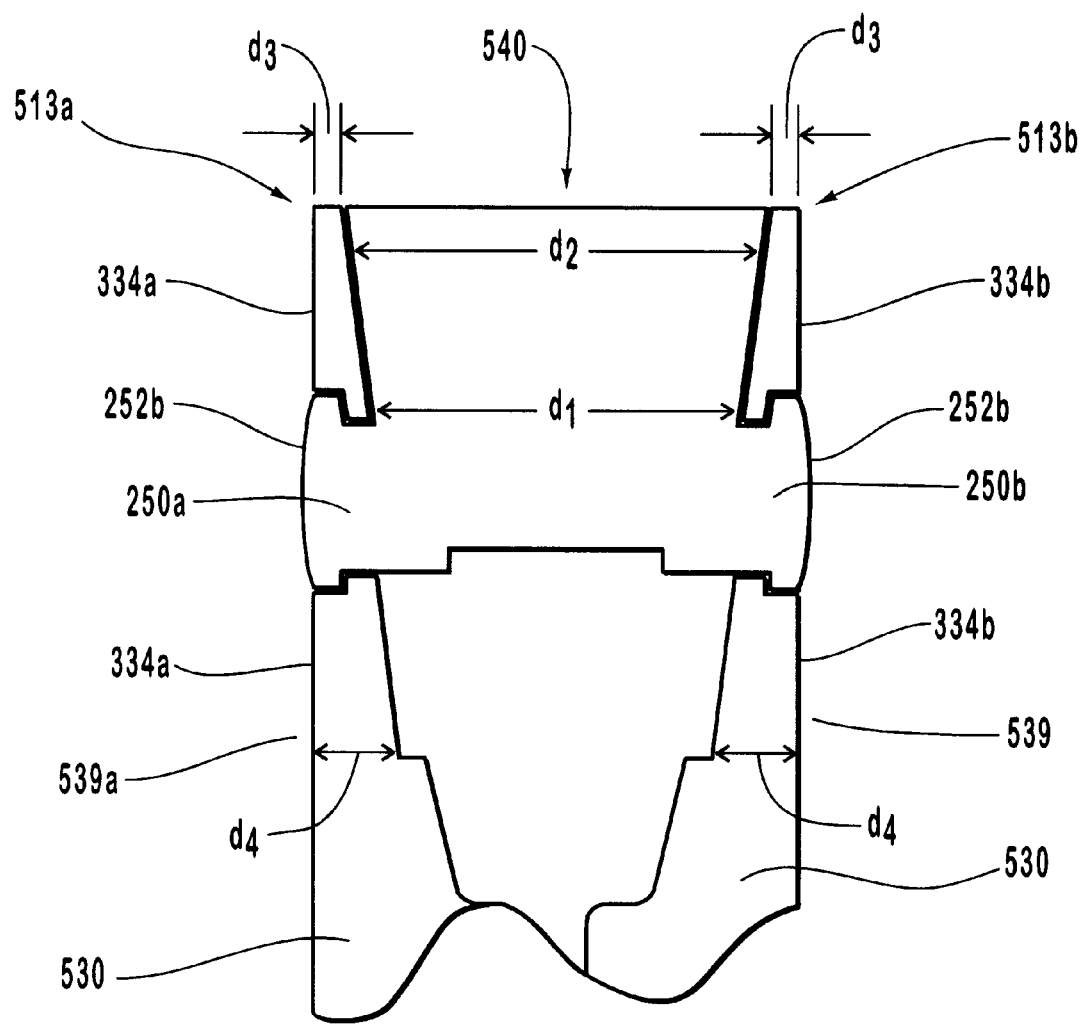
FIG. 15C is a slightly out-of-centroid cross-section elevational view of the dental matrix retainer clamp depicted in FIG. 15A in which it can be seen that the main body element at the flange end is in engagement with the head element and in which it can be seen that the flange and the head element have complementary cross-sectional shapes.

FIG. 15C is an elevational cross-section view of dental matrix band holder 520 depicted in FIG. 15A. The view is taken slightly away from the centroid of head element 540 along the line 15A–15C, such that guide slot 546 is not exposed. Therein, it can be seen that head element 540 has the two dimensions $d_1$ and $d_2$ seen in FIG. 15A. It can be seen that $d_1$ is less than $d_2$ such that head element 540 has a wedge shape wherein $d_1$ is the smaller dimension of the wedge. The opposed flange members 534 of the main body element 530 also have two dimensions $d_3$ at stop ends 537 of the opening defined by opposed flange members 534 and $d_4$ at the stop portion 539 of the opening defined by opposed flange members 543. It can be seen that $d_3$ is smaller than $d_4$ such that opposed flange members 534 also have a wedge shape. It can be seen that head element 540 with its wedge shape is complimentary and opposite to opposed flange members 534 with their wedge shapes. Thereby, rotation of head element 540 downwardly such that $d_2$ is rotated near $d_4$ causes increasing resistance between head element 540 and opposed flange members 534. The increasing resistance is proportional to the degree of rotation away from a neutral position depicted in FIG. 15A. Additionally, friction between opposed flange members 534 and head element 540 may be enhanced by creating a roughened surface where head element 540 and opposed flange members 534 slidingly make contact with each other. Alternatively, only one of head element 540 and opposed flange members 534 need have the wedge shape. The advantage of this embodiment is that the dental professional's view and the beam of a dental curing light is substantially unobstructed by head element 540.

It is notable that head element 540 is shown having similarities in configuration to head element 240 such as opposed supporting shoulders 241 and 541. However, any head element may be used which is configured to provide a wedge fit with opposed flange members in any above-depicted embodiment and the like. Thus, a head element, by way of non-limiting example may have an $r_3$ dimension as the largest dimension, and slidingly make contact along a wedge-shaped interface such as that indicated in head element 540 in contact with opposed supporting shoulders 541. Additionally, like the other head elements such as head element 440, head element 540 may have a characteristic dimension which in a ratio that is no greater than about 2:1 to a common characteristic dimension of each flange member 534. Similarly, the ratio may range from being no greater than about 1.75:1 and no less than about 1:1, as in other embodiments In addition to being used with any suitable dental matrix band holder, the inventive dental matrix band may be used with any dental wedge. For example, the dental matrix band may be used with any prior art dental wedge such as those shown in FIGS. 3–5. Similarly, dental wedges such as those disclosed in U.S. Pat. No. 5,743,738 issued to Baffelli et al. and U.S. Pat. No. 5,421,725 issued to von Weissenfluh may be used. These U.S. patents are hereby incorporated by specific reference. The wedge may be made from wood or from other suitable materials such as plastic. The wedge may be opaque, entirely translucent or only a portion thereof may be translucent such as the body to enable light to be directed through the wedge.

The dental matrix band is preferably used with a wedge as disclosed in U.S. Pat. No. 5,890,900 and U.S. Pat. No. 5,890,901 both which issued to Dan E. Fischer and are assigned to Ultradent Products, Inc. The wedges are also disclosed along with related tools in U.S. patent application Ser. No. 09/064,457 entitled Dental Instruments for Use with Dental Wedges which was filed on Apr. 22, 1998 on behalf of Dan E. Fischer. This application and the two U.S. patents are also hereby incorporated by specific reference. An example of such wedges, as disclosed in these references, are discussed hereinbelow and are shown in FIG. 7D and 16A–16J at 630. Other embodiments are shown in FIGS. 17–21 as well.

The wedges have various gripping and non-slip surfaces which enable a practitioner to achieve a suitable grip, retain the wedge in a desired, fixed position with respect to a dental instrument, and safely position the dental wedge between teeth. The gripping and non-slip surfaces also enable a practitioner to remove the wedge upon completion of a dental procedure by grasping the wedge with a dental instrument and then pulling without the dental instrument slipping off wedge.

As shown in FIGS. 7D and 16A–16J, a dental wedge 630 of the present invention is comprised of (i) a body 640 having a distal insertion end 642 and a proximal end 644; and (ii) a head 660 coupled to body 640, head 660 having a distal end 662 and a proximal end 664. Also as shown, a neck 650 preferably couples head 660 to body 640. The similar or identical elements of the other embodiments of dental wedges of the present invention shown in FIGS. 17–21 are identified with the same numerals unless indicated otherwise.

As shown, distal end 652 of neck 650 is coupled to proximal end 644 of body 640. The proximal end 654 of neck 650 is coupled to distal end 662 of head 660. Wedge 630 has a longitudinal axis demonstrated by line 658 shown in FIG. 16C.

Figure 16A:
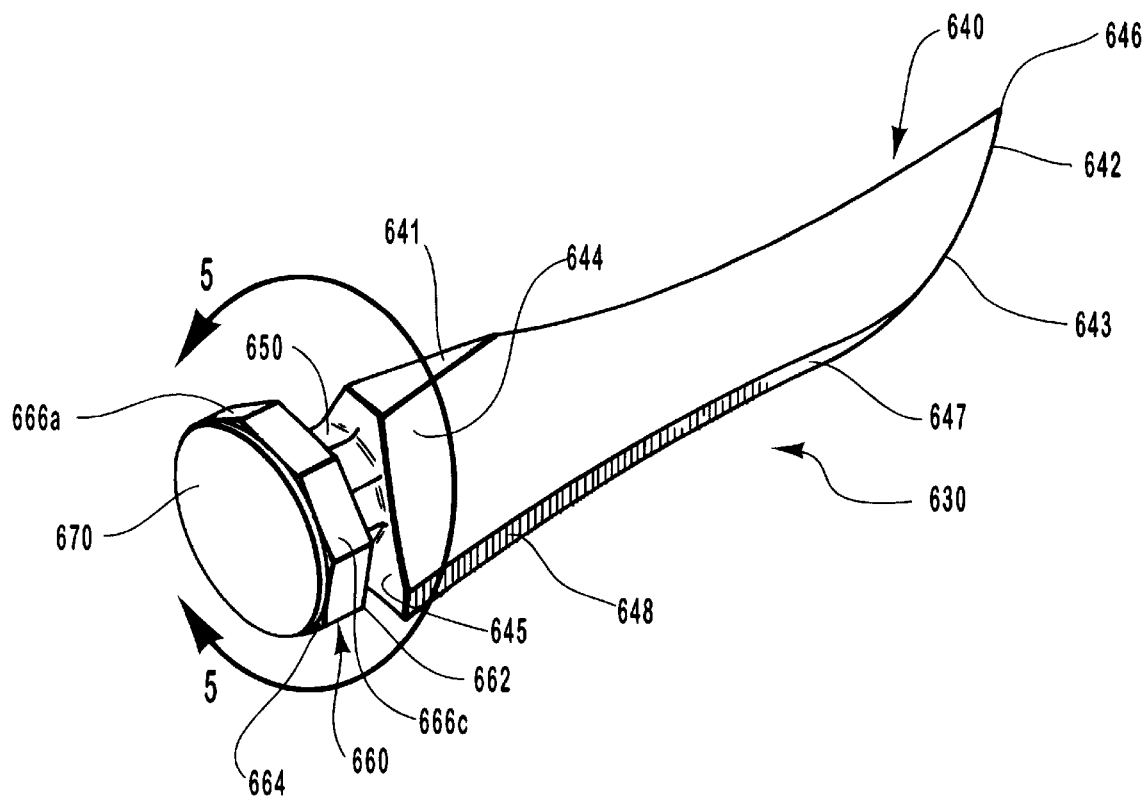
FIG. 16A is a perspective view of a dental wedge of the present invention.

The body of the wedge may have any configuration suitable for insertion into an embrasure or within an interproximal space between two teeth. As shown in FIG. 16A, the preferred configuration of the body of the wedge generally has a relatively thin distal insertion end with a bottom portion 643 that is relatively curved and which terminates at a pointed tip 646. The body preferably flares from the distal insertion end toward the proximal end 644 such that the body has a triangular cross-section of increasing size. The thin distal portion permits the practitioner to initially dispose wedge 630 between the patients' teeth. The taper of body 640 enables a practitioner to move teeth relative to each other as pressure is exerted on the wedge. More specifically, as the wedge is pushed inward, the cross section of the wedge between the teeth becomes increasingly wider, thereby enabling relative teeth movement.

As shown, body 640 is preferably not entirely triangular in cross-sectional shape as the opposing comers of the base of the triangle have been truncated to provide spacing sides 647 which provide increased leverage in separating or displacing teeth. Note that the apex has been partially truncated at proximal end 644 to yield truncated apex 641. Other embodiments such as the wedge bodies shown in FIGS. 16E–16F at 640*b* and in FIG. 18 at 740 are not truncated so that the sides all terminate at comers.

Figure 16B:
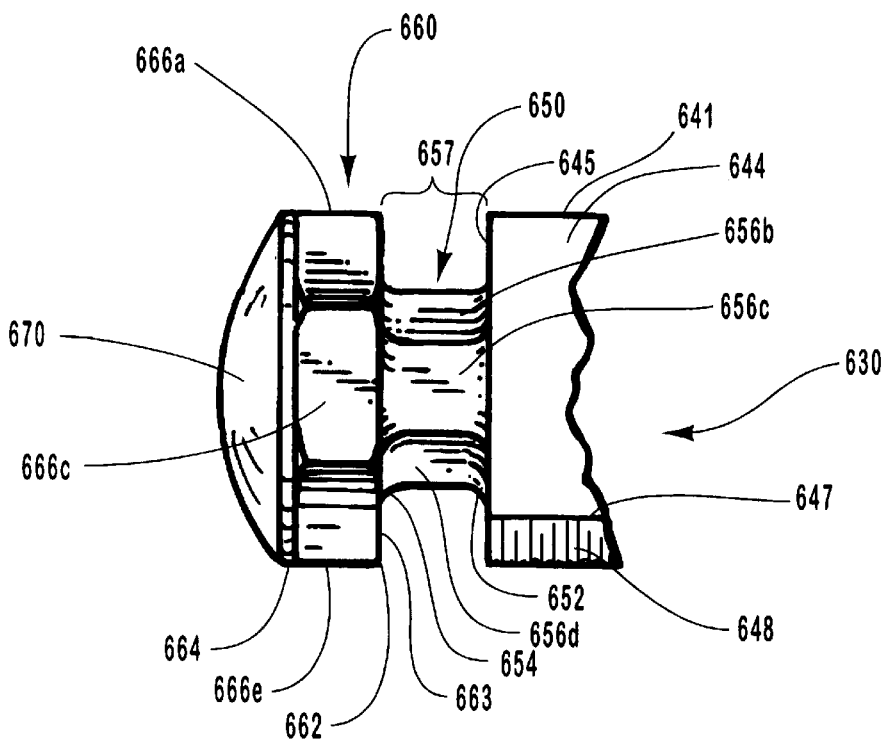
FIG. 16B is an enlarged side view of the head and neck of the wedge shown in FIG. 16A.
Figure 16C:
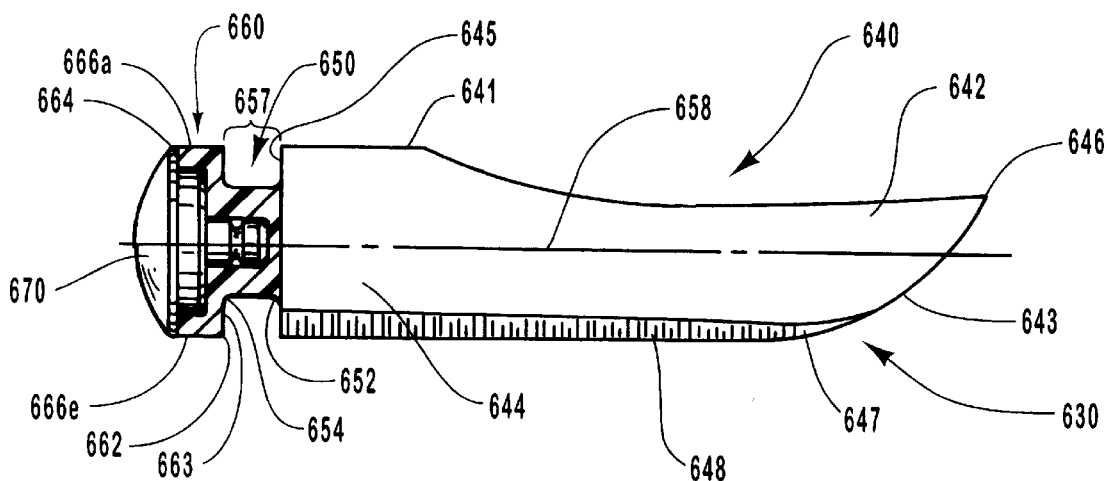
FIG. 16C is a side view of the neck and head of the dental wedge of FIG. 16A with a partial cut-away cross-sectional view of the neck and head.
Figure 16D:
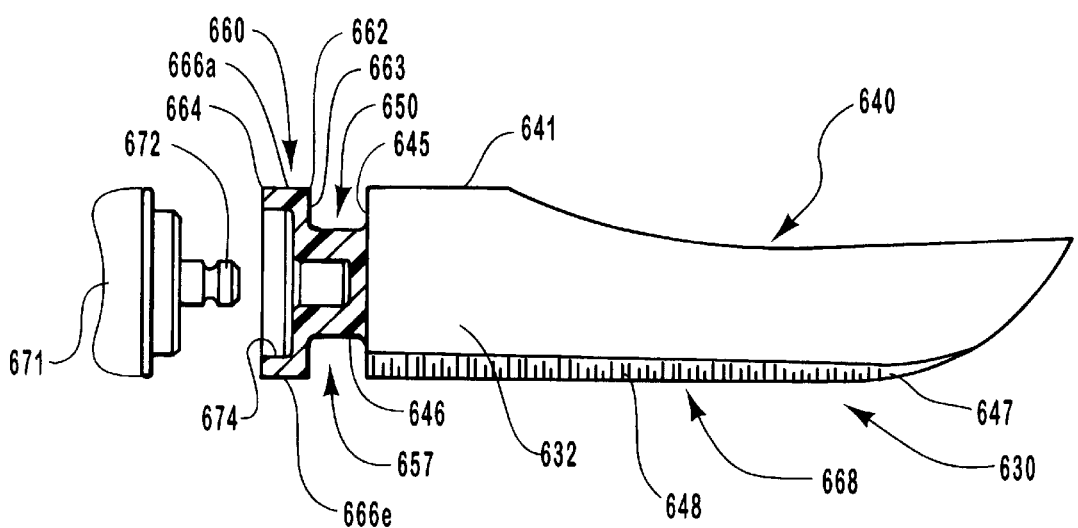
FIG. 16D is an exploded view of the embodiment shown in FIGS. 16A–16C which depicts the cap detached from the proximal end of the head of the dental wedge. The dimpled cap depicted in FIG. 16D is a different embodiment of a cap.

As previously discussed, separation of the teeth enables a practitioner to position a matrix band around a tooth. As also discussed above, disposing a wedge between the patient's teeth against a matrix band helps to ensure that the matrix band is held against the prepared tooth. The friction provide by the frictional engagement surface of a matrix band is enhanced when the pushing sides are configured with a frictional resistance surface. The frictional resistance surface of pushing sides 647 is identified at 648 as being ridges so that pushing sides 647 have a serrated appearance. The ridges can be separated by any suitable length and can have any suitable height. The ridges are preferably formed when the wedge is molded. Note, however, that the pushing sides need not necessarily be configured with a frictional resistance surface as shown in FIG. 16H at 647*c*.

Figure 20:
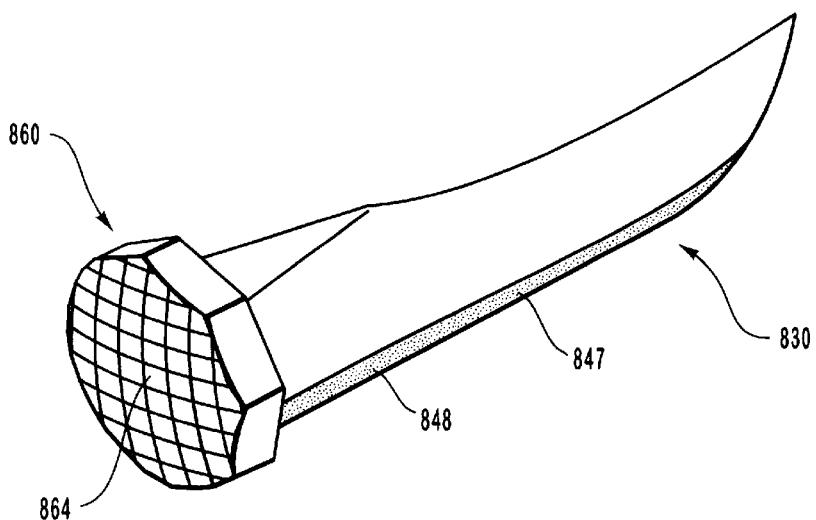
FIG. 20 is a perspective view of another embodiment of a dental wedge of the present invention which has no neck and a body which is integral with the head. The head has a textured proximal end.
Figure 21:
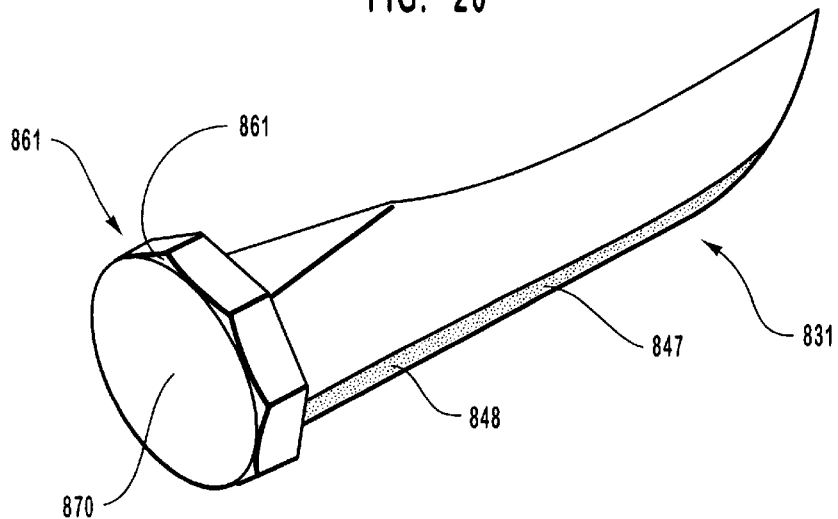
FIG. 21 is a perspective view of another embodiment of a dental wedge of the present invention which has no neck and a body which integral with the head. The head has a smooth proximal end.

In addition to ridges, the frictional resistance surface of the dental wedge may be a roughened surface like that of the dental matrix band and may be formed by the same methods. Further, the frictional resistance surface of the dental wedge may be formed by any method used to form the frictional engagement surface of the dental matrix bands. An example of a dental wedge with pushing sides having a roughened frictional resistance surface is shown in FIGS. 20–21 at 848. The frictional resistance surface of the dental wedge may also extend beyond the pushing sides such that the frictional resistance surface covers the entire body of the wedge or portions of the body. Any dental wedge may be configured with such a frictional resistance surface and be within the scope of the present invention. The frictional resistance surfaces of dental wedges disclosed herein are examples of means for preventing a dental wedge from coming out of an embrasure after being pushed into an embrasure against a dental wedge.

Figure 16E:
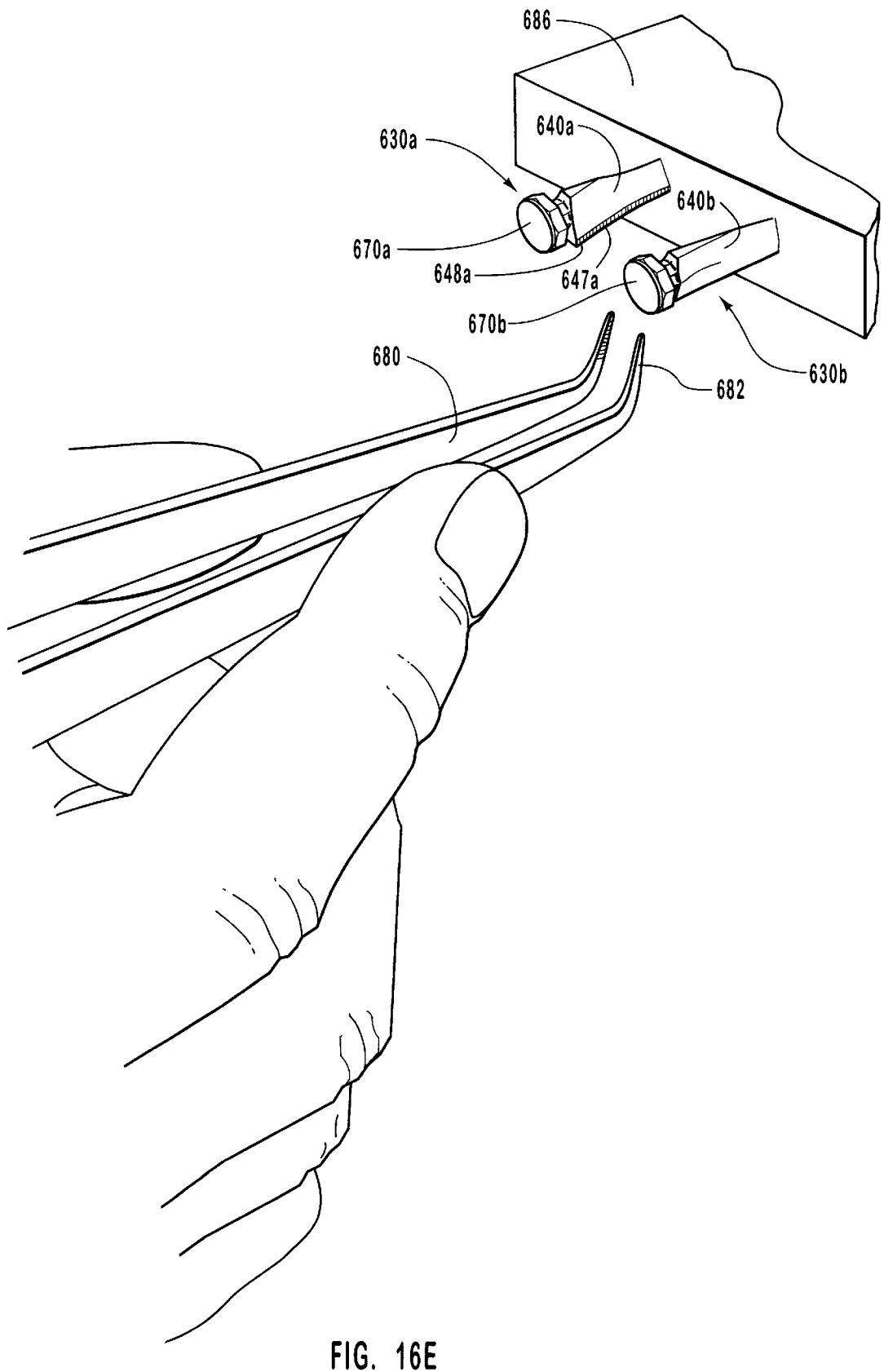
FIG. 16E is a perspective view of a user selecting a dental wedge from a set of dental wedges with different flares.

As shown in FIG. 16E, a kit may be provided of at least two wedges and the wedges may have differing configurations. More particularly, the bodies of the wedge may have different flares or tapers as depicted in FIG. 16E at 640*a* and 640*b*. Bodies 640*a* and 640*b* of wedges 630*a* and 630*b* each have a triangular cross section, however, body 640*a* has a wider base and apical angle than does body 640*b*. In addition to the width of the base, the pitch or apical angle, the bodies of the wedges may also have differing heights. The various embodiments of wedge bodies disclosed herein, including the prior art body configurations discussed hereinabove, are examples of tapered body means for insertion within an interproximal space between two teeth. Additionally, any conventional body configuration may also be utilized.

Note that wedges 630*a* and 630*b* FIG. 16E are shown standing upright in a support material 686 which is preferable for maintaining the wedges in a sterile or nearly sterile condition. As shown in FIG. 16E, a user can easily grasp a wedge with the prongs 682 or grasping end of conventional cotton pliers 680.

Figure 16F:
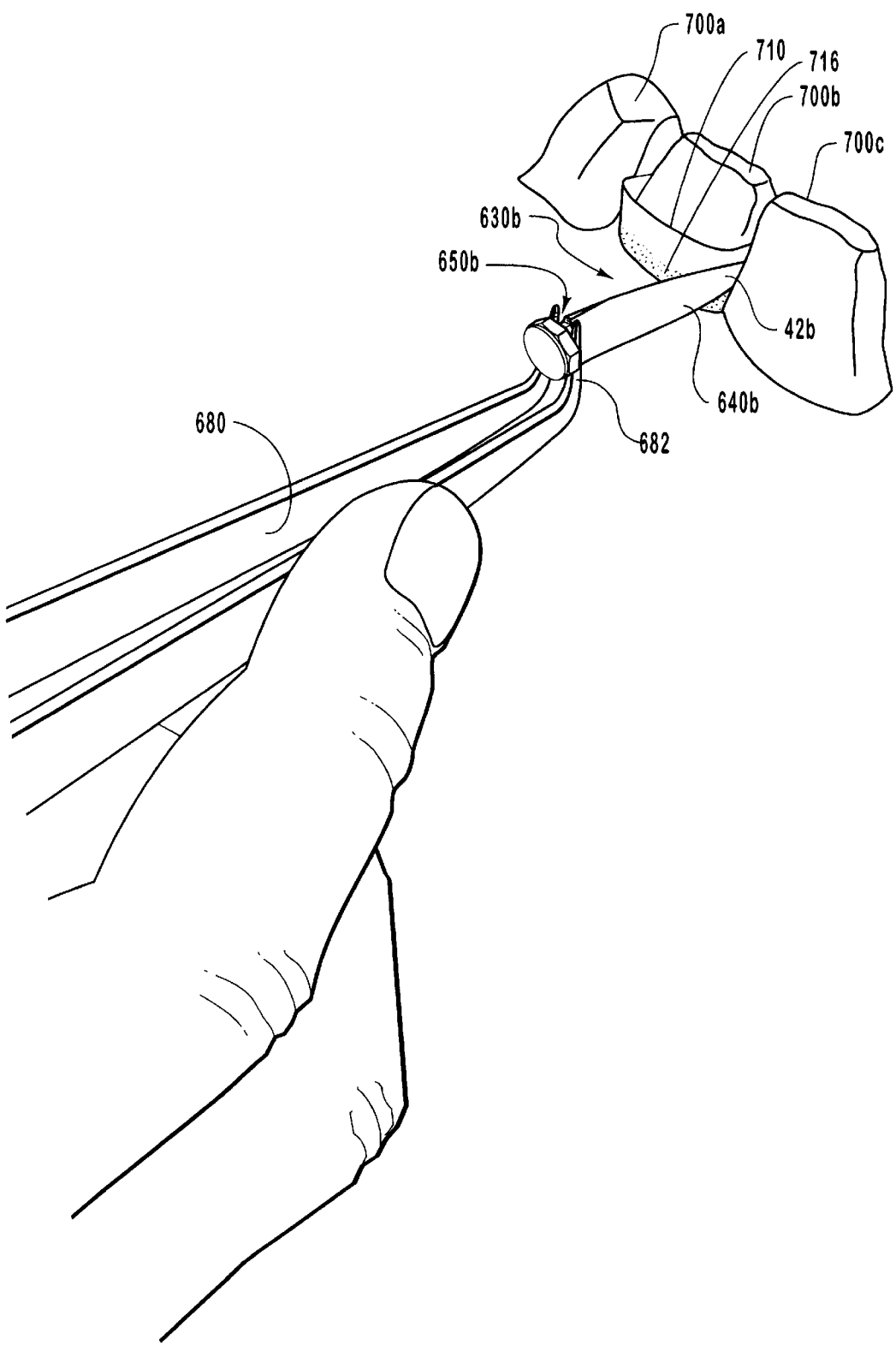
FIG. 16F is a perspective view of a user's hand grasping a dental wedge by the neck of the dental wedge with cotton tweezers and inserting the distal insertion end of the dental wedge into an embrasure or interproximal space adjacent a matrix band disposed about a tooth.
Figure 16G:
FIG. 16G is a perspective view of a user's hand pushing on the head of a dental wedge with the blunt end of cotton tweezers to further insert the dental wedge between the teeth.
Figure 16H:
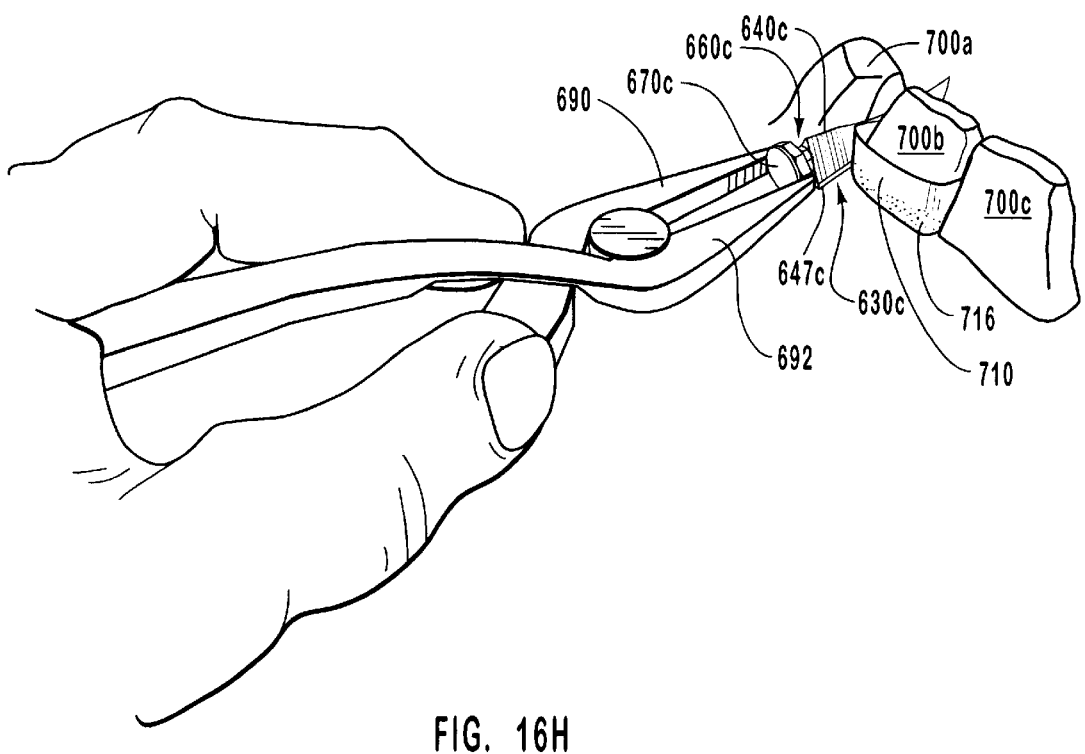
FIG. 16H is a perspective view of a user's hand pulling on the head of a dental wedge with pliers to remove the dental wedge from between the teeth.

FIGS. 16F–16H shows the combined use of various dental wedges and a matrix band 710 having a frictional engagement surface 716. As noted above, these dental wedges help to ensure that matrix band 710 is held against the prepared tooth, particularly dental wedge 630*a* shown in FIG. 16G which has pushing sides 647*a* with frictional resistance surface 648*a*. Note that matrix band 710 is shown in FIGS. 16F–16G without a dental matrix band holder primarily to enhance the viewability of the wedges; however, as discussed above in reference to FIG. 7D the wedges are preferably used with a dental matrix band holder. The matrix bands depicted in FIGS. 16F–16D are examples of matrix band which have ends that are held together by various conventional methods including spot welding, soldering or the use of an elastic band, such that the band forms a sleeve or a form about the tooth. Note that solder, elastic bands and spot welding are further examples of means for positioning a matrix band around a tooth to enable the matrix band to be used in filling a dental preparation. Such structures are also, more specifically, examples of means for maintaining a matrix band around a tooth after the matrix band has been positioned for filling a dental preparation.

FIG. 16F shows prongs 682 grasping wedge 630*b* by neck 650*b* as distal insertion end 642*b* is being pushed into an interproximal space. The base or widened end of the wedge is located toward the gum line and the thin apex extends between the teeth 700 and away from the gums. The body can be initially inserted or pushed completely into position by grasping the neck and/or by pushing against the face of the proximal end of the body, such as face 645 shown in FIG. 16A and FIG. 16B at 645. One preferred technique for pushing the body of a wedge completely into position is depicted in FIG. 16G wherein the blunt end 684 of conventional cotton pliers 680 is shown being utilized to push body 640*a* of wedge 630*a* further between the teeth. A wedge can be easily removed by pulling while grasping the neck as shown in FIG. 16F with prongs 682 of tweezers 680 and/or by pulling against the face of proximal end of the head, such face 663 shown in FIG. 16B at 663. Additionally, a wedge may be removed from an embrasure by grasping the head with conventional cotton tweezers or as is shown in FIG. 16H the head 660*c* of a wedge 630*c* may be grasped and pulled with the grasping end 692 of pliers 690. While the instruments disclosed in FIGS. 16F–16H for inserting and removing the dental wedges are acceptable, inventive instruments which are particularly adapted for use with the inventive dental wedges are also disclosed in U.S. patent application Ser. No. 09/064,457 referenced above.

As best shown in FIGS. 16A–16B, neck 650 has a smaller diameter than distal end 662 of head 660 and proximal end 644 of body 640, thereby forming a groove 657 for placement of a dental instrument therein. Groove 657 is defined by (i) proximal end 644 of body 640; (ii) the exterior surface of neck 650; and (iii) distal end 662 of head 660. Essentially, the reduced diameter neck 650 is any depression or groove located between the head and the proximal end of the face.

Figure 16I:
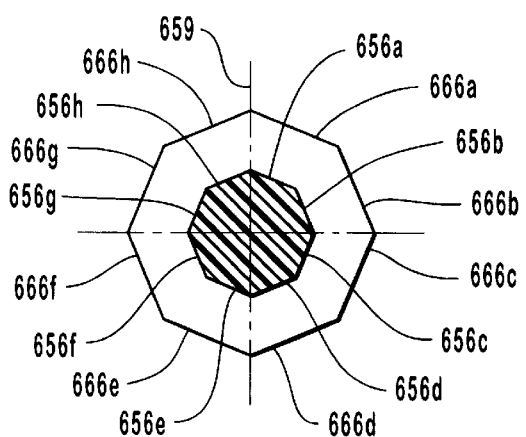
FIG. 16I is a cross sectional view of a head and neck of the dental wedge of FIG. 16A and FIG. 16B, the flat surfaces of the head being aligned along an axis with the flat surfaces of the neck.

FIGS. 16A–B and FIG. 16I also depict neck 650 having eight different flat gripping surfaces 656a–h extending about the circumference of the surface of the neck, such that a transverse cross section of neck 650 has the shape of an octagon. The neck preferably has eight different flat gripping surfaces as shown at 656a–h, however, the neck may have any suitable configuration. For example, the neck may have a cross-section which is generally circular, elliptical, triangular, or the neck may have four or more different flat gripping surfaces extending about the circumference of the surface of the neck such that the cross-section is that of a square, a pentagon, a hexagon, a decagon and so on. Even numbers of flat surfaces are preferred for the neck, but not required. Nevertheless, neck 650 preferably includes the shape of a polygon having more than four sides. As a result of the multiple surfaces on neck 650, neck 650 may be grasped from a variety of different gripping angles and positions. Additionally, the circumference of neck 650 is preferably symmetrical.

Each neck disclosed herein is an example of neck means for receiving a grasping end of a dental instrument to move the tapered body means with respect to an interproximal space between two teeth, and for coupling the distal end of the head means to the proximal end of the tapered body means. In alternative embodiments, the surface of the neck may be textured or coated with a tacky material. Additionally, a flexible and compressible washer may be positioned around the neck. Such texturing, coatings and washers are examples of means for preventing slipping of a dental instrument urged against the wedge, or more specifically a dental instrument used to grasp the wedge or neck.

Like neck 650, head 660 is also shown in FIGS. 16A–16B and in FIG. 16I with eight different flat sides at 666a–h. The head may have any suitable configuration, however, the head preferably is in the shape of a polygon with more than four different flat sides extending about the circumference of the head. Examples of such shapes include a pentagon, hexagon, octagon, a decagon and so on. Thus, the cross section of head 660 transverse to axis 658 may be in the shape of a pentagon, hexagon, octagon, decagon and so on. As shown, the circumference of head 660 is preferably symmetrical since each flat side has the same dimensions. While not required, the number of different flat gripping surfaces 666 of head 660 is preferably even, such as six, eight, ten, and so on as it is for flat gripping surfaces 656 disposed about the circumference of neck 650.

Figure 4:
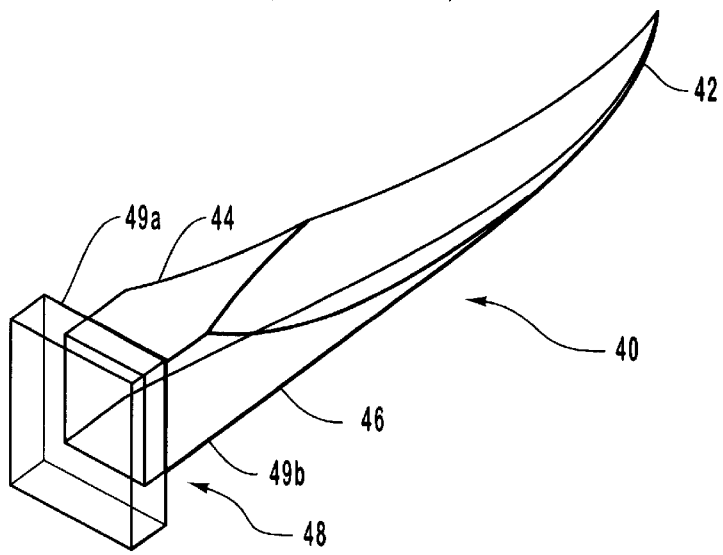
FIG. 4 is a view of another dental wedge of the prior art.
Figure 5:
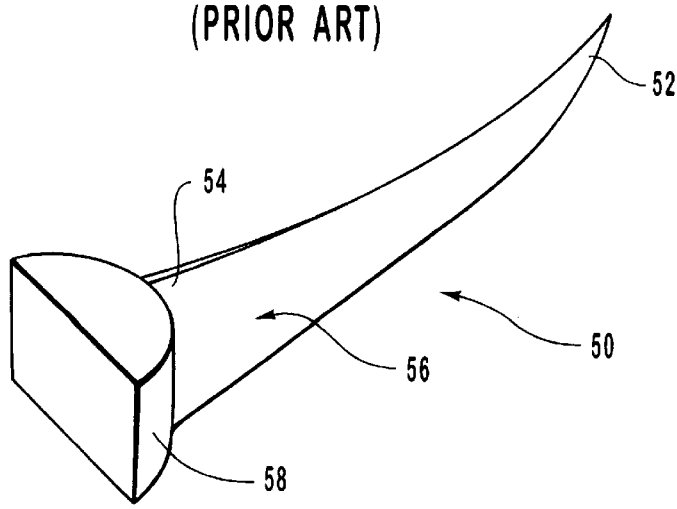
FIG. 5 is a view of yet another dental wedge of the prior art.

Thus, rather than having limited gripping angles, as is the case with a square shaped head 48 of FIG. 4, head 660 has many different gripping angles. Since some gripping angles may not be accessible due to the location of the embrasure into which the wedge is being positioned, it is preferable to have a high number of choices for the gripping angle. Accordingly, the transverse cross section is preferably that of a hexagon, an octagon, a decagon, and so on to provide a large number of different gripping angles.

It will be appreciated that each gripping angle corresponds to a number of different gripping positions. For example, if a practitioner grips the top and bottom surfaces 666a and 666e of head 660, as shown in FIG. 16B and FIG. 16D, which is an example of one gripping angle, the practitioner's hand may be oriented in a variety of different positions while holding tweezers or pliers. In the octagonal embodiment, for example, a practitioner's pliers can grip the top and bottom surfaces 666a and 666e or any other combination of opposing surfaces. As a result, when reaching from an awkward position into the mouth, a practitioner is more likely to achieve a suitable grip, to retain wedge 630 in a desired, fixed position in a dental instrument, and to sufficiently position dental wedge 630 between teeth.

FIG. 16I is a cross sectional view of head 660 and neck 650 of wedge 630 shown in FIG. 16B. In the embodiment shown in FIG. 16I, the flat surfaces 666a–h extending about the circumference of head 660 and the flat surfaces 656a–h extending about the circumference of neck 650 are aligned with each other along an axis 659. Accordingly, any two opposing sides such as 666b and 666f or 656c and 656g may be easily grasped.

Figure 16J:
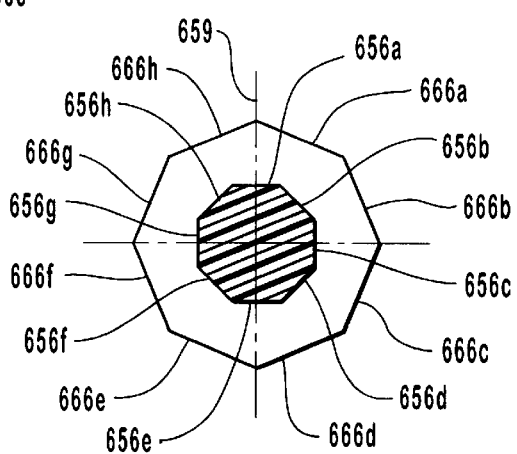
FIG. 16J is an alternative cross sectional view of the head and neck of a dental wedge, the flat surfaces of the neck being offset from the flat surfaces of the head.

In another embodiment of a dental wedge shown in FIG. 16J, the head and the neck each have a plurality of flat surfaces respectively identified at 666a–h and 656a–h. Flat surfaces 666a–h of the head and the flat surfaces 656a–h of the neck are offset with respect to flat surfaces each other such that 666a is not parallel with 656a as in the configuration shown in FIG. 16I.

By offsetting the respective gripping surfaces 666a–h and 656a–h respectively of the head and neck as shown in FIG. 16J, it is possible to create even more gripping angles than are available individually on the embodiment shown in FIG. 16I. The increased number of gripping angles and positions created by the offset nature of the head and neck is a significant advance within the art. Although, the embodiment shown in FIG. 16J offers greater gripping angles which makes it easier to push or pull the wedge, the embodiment shown in FIG. 16I is easier to mold.

When reaching through the fixed diameter of the mouth to typical wedges, a practitioner may not have the option of twisting the tweezers or pliers along one of two angles to grasp a four-sided head, such as head 48 shown in FIG. 4. If more than two gripping angles are available, however, such as shown in FIGS. 16I and 16J, a practitioner's chances are vastly improved of securely grasping a wedge as needed, It will be appreciated that in addition to grasping head 660 and/or neck 650, the practitioner may also grip body 640 as well.

Because of the various surfaces of the wedge, the practitioner has the option of grasping and pulling, grasping and pushing, or pushing against a variety of different structures on the wedge 630. Additionally, the head and neck may be grasped from a variety of different positions around the circumference thereof. In a preferred method of using the wedge, prongs or grasping end 682 of tweezers 680 are used to grasp neck 650 and initially position the wedge into an embrasure as shown in FIG. 16F. More specifically, prongs 682 are pushed against proximal end 644 of body 640 or are used to firmly grasp neck 650 while pushing against proximal end 644 to push wedge 630 into a desired location. The body of the wedge is then fully inserted into position as shown in FIG. 16G by urging the blunt end 684 of tweezers 680 against head 660. Removal is preferably accomplished in the same manner shown in FIG. 16F for initial placement by gripping neck 650 and then pulling the wedge out of the embrasure. More specifically, wedge 630 may be pulled from the embrasure by pulling against the distal end 662 of head 660 with prongs 682, by firmly grasping neck 650 and pulling, or by grasping neck 650 while pulling against distal end 662.

Figure 17:
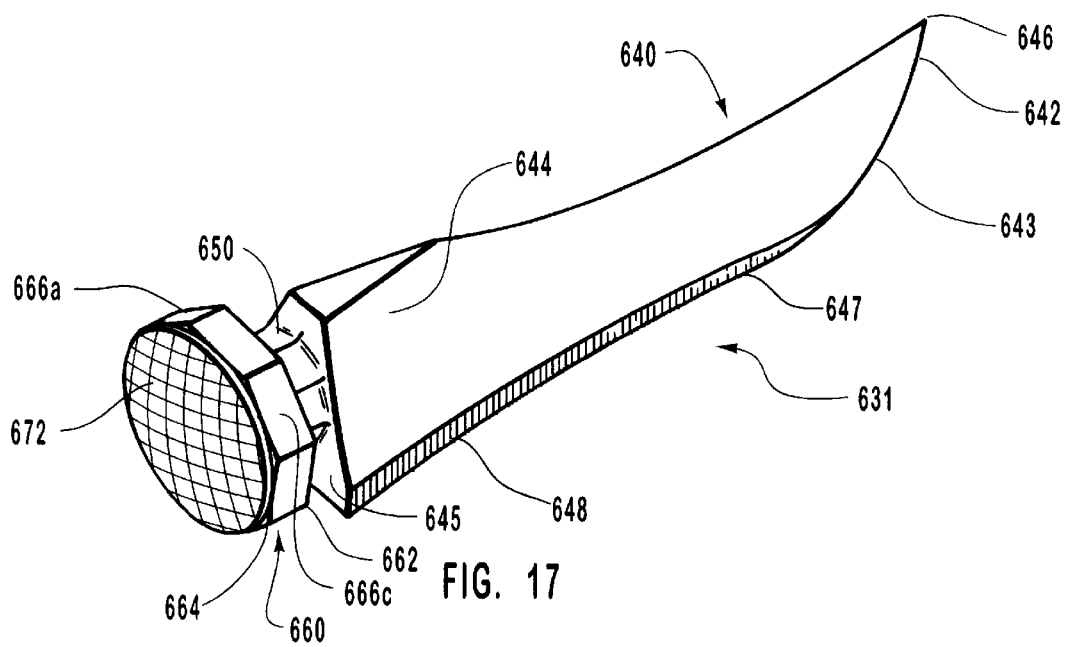
FIG. 17 is a perspective view of another embodiment of a dental wedge of the present invention which has a head with a textured cap or proximal end.

FIGS. 16A–16C and 16E–16H depict proximal end 642 as having a cap 670. Other embodiments of caps are shown in FIG. 16D and FIG. 17 respectively at 671 and 672. As shown most clearly in FIG. 16D, each cap preferably has an insertion prong 673 which fits into a chamber 674 extending through head 660 and neck 650. Insertion prong 673 is an example of an attachment means for attaching a cap to a head which is adapted to receive a cap. Another example of an attachment means is adhesive. The adhesive may be applied between the cap and a head with a shape that is adapted to be mated with the opposing surface of the cap. Such mated surfaces include flat surfaces.

Caps 670, 671 and 672 are preferably comprised of a material, such as an elastomer, which is resilient and which compresses when pushed or gripped. Although any suitable material may be used, caps 670, 671 or 672 are preferably formed from elastomers such as neoprene, silicone, polyurethane, polypropylene, latex, rubber, etc.

When pushed with the blunt end 684 of tweezers as shown in FIG. 16G, cap 670 compresses, avoiding a slippery dynamic which may result with a rigid surface. Rather than sliding on a rigid surface, blunt end 684 of tweezers 680 indents into the resilient, compressible material. As best viewed in FIG. 16C, cap 670 has a convex surface as more compressible material is disposed in the center of the convex surface than on the periphery. By enabling the cap to indent, the surface area contacted by the instrument is increased thereby decreasing the potential for slipping.

While cap 670 is essentially convex, cap 671 is essentially concave or dimpled. By positioning a dental instrument at or near the low point in dimpled cap 671, the concavity assists in preventing a dental instrument from slipping off of cap 671. The concavity can be relatively shallow or relatively deep.

The textured surface of cap 672 shown in FIG. 17 of wedge 631 provides even greater resistance against slipping as a user pushes an instrument against the cap than does a compressible cap with a smooth surface such as cap 670. The textured surface of cap 672 is formed to have raised surfaces or is roughened to prevent dental instruments from sliding across the surface. The textured surface could be, for example, comprised of knurls, cuts, grooves, or other texturing such as chemical etching or gritblasting. Textured surfaces may be utilized on any cap configuration. For example, a concave cap such as cap 671 may be configured with a textured surface such as cap 672.

Each cap disclosed herein is an example of a non-slip surface or means for preventing slipping of a dental instrument urged against the wedge, or more particularly to prevent slipping of a dental instrument when pushing against head 660. Another example of a non-slip surface or means for preventing slipping of a dental instrument is a cap such as cap 670, 671 or 672 which has been coated with a relatively tacky material.

Figure 18:
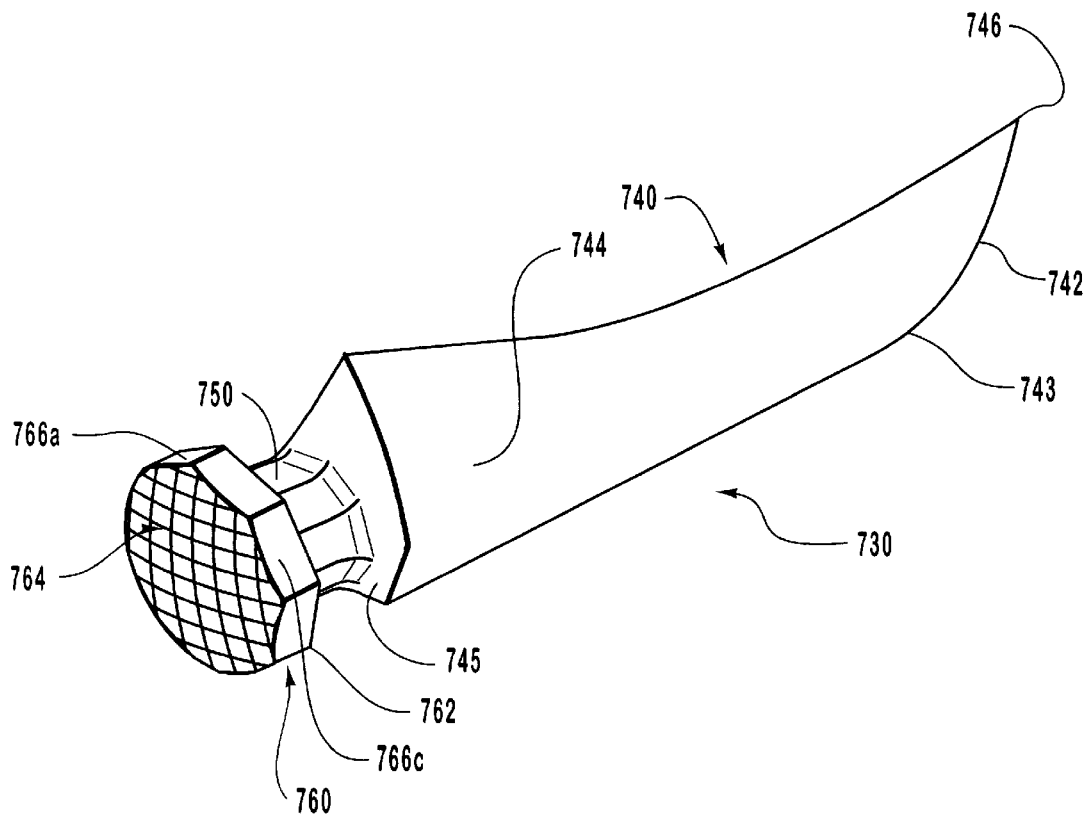
FIG. 18 is a perspective view of another embodiment of a dental wedge of the present invention which has an integral head with a textured proximal end.

FIG. 18 depicts a wedge at 730 with a head 760 having a proximal end 764 which is textured. The textured surface of proximal end 764 is another example of means for preventing slipping of a dental instrument. The compressible caps 670, 671 and 672 used with wedge 630 provide greater resistance to slipping, however, wedge 730 can be more easily manufactured as it is entirely one component.

Figure 19:
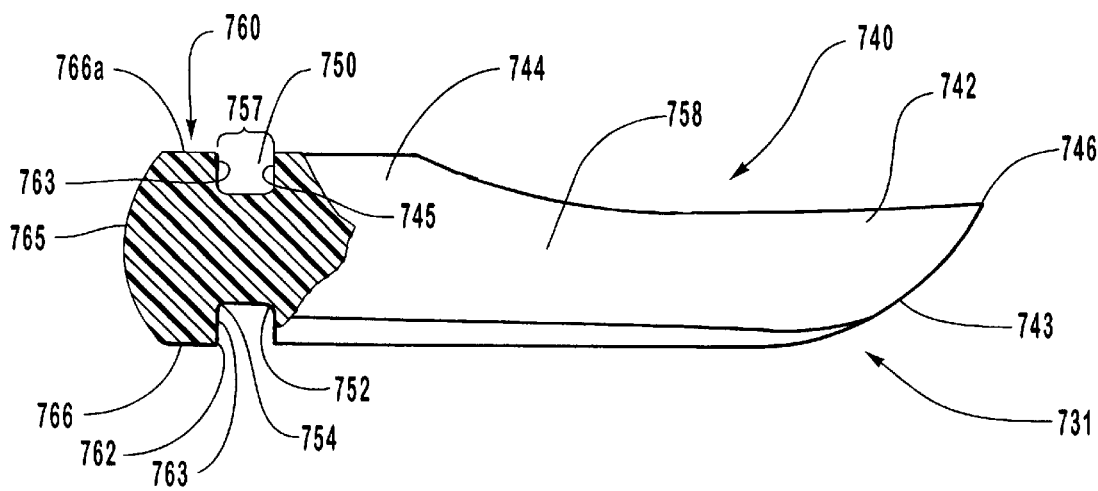
FIG. 19 is a perspective view of another embodiment of a dental wedge of the present invention which has a head with a textured proximal end.

FIG. 19 depicts another embodiment of a dental wedge of the present invention at 731. Head 760 of wedge 731 has a proximal end 765 which is smooth and does not have a cap. Like wedge 730, wedge 731 is also entirely integral and accordingly less expensive to manufacture than wedges 630 or 631. Proximal end 765 of wedge 731 and also proximal end 764 of wedge 730 may be coated with a relatively tacky material to provide increased resistance to slipping. A coating on either proximal end 764 or 765 provides another example of means for preventing slipping of a dental instrument.

As shown in FIG. 20 and FIG. 21, some embodiments of the present invention have a head directly coupled to the body without a neck. In such embodiments, the head is preferably larger than the body as are heads 860 and 861 of respective wedges 830 and 831 depicted in FIG. 20 and FIG. 21. Similarly, the heads of the wedges in the other embodiments may also be larger than their respective bodies. Wedge 830 is entirely integral as there is no cap. Proximal end 864 of head 860 is configured with a textured surface to minimize the potential for a dental instrument to slip while being urged against the instrument or as the instrument is pushed against the proximal end. Proximal end 865 of head 861 has a cap 870 which is formed from the same material as caps 670, 671 and 672. Cap 870 has an insertion prong (not shown) which fits into a chamber (not shown) in the body. Cap 870 may have any suitable configuration such as a convex shape as shown or a concave shape. Additionally, cap 870 may also be textured. Further, cap 870 and proximal end 864 may also be coated with a relatively tacky material to minimize slipping of dental instruments.

Since the body of the wedges is configured to be disposed within an interproximal space and to maintaining a matrix band in a desired orientation between adjacent teeth or otherwise maintaining a space between teeth, the body is preferably comprised of a rigid material, such as a relatively rigid plastic. The individual components of the wedges or the integral wedges can be formed by any means, such as thermoplastics or cast plastics formation techniques. One skilled in the art will appreciate that a variety of different methods are available for manufacturing the dental wedges. In the embodiments, wherein the wedge is entirely integral, the wedge may be molded from plastic into a rigid wedge and even be translucent. In the embodiments, wherein the wedge comprises two components, an integral component and a cap configured to interlock within a chamber in the neck and head of a wedge. The integral component is a body, neck and at least a portion of the head; all of these may be translucent. The cap is preferably separately formed into a resilient, compressible component which interlocks with a separately formed rigid component. The two components may be designed to interlock through the configuration of the insertion prong of the cap and the chamber. In yet another embodiment, the two components are molded to each other, such as by using a two-color mold to cause the components to chemically adhere to each other. Additionally, an adhesive may be placed between the two components such as thermal adhesive glue, an adhesive coating, an adhesive pad, and a pressure sensitive adhesive. The dental wedges disclosed herein may be provided as kit or system with the inventive dental matrix band alone or also with a dental matrix band holder.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A matrix band comprising:
   a flexible strip having a first end opposite a second end and a top edge opposite a bottom edge, wherein the flexible strip has an elongated and slightly curved configuration such that when the ends are joined together the matrix band has a midsection which is scooped to enable the matrix band to anatomically conform to a tooth when positioned around a tooth requiring restoration, the flexible strip having opposing sides including an interior side and an exterior side, wherein the interior side is smooth for contact with the surfaces of a tooth requiring restoration and for contact with the restoration, wherein the exterior side has at least a portion of its surface configured as a frictional engagement surface to provide frictional engagement with a dental wedge pushed against the frictional engagement surface, wherein the frictional engagement surface of the exterior side is significantly rougher and more abrasive than the interior side.

2. A matrix band as recited in claim 1, wherein the frictional engagement surface of the exterior side extends from the bottom edge upward toward the top edge at least one-third of the distance between the bottom edge and the top edge.

3. A matrix band as recited in claim 1, wherein the frictional engagement surface of the exterior side extends from the bottom edge upward toward the top edge at least one-half of the distance between the bottom edge and the top edge.

4. A matrix band as recited in claim 1, wherein the frictional engagement surface covers all of the surface of the exterior side.

5. A matrix band as recited in claim 1, wherein the frictional engagement surface extends continuously from the first end to the second end.

6. A matrix band as recited in claim 1, wherein the frictional engagement surface extends intermittently from the first end to the second end.

7. A matrix band as recited in claim 1, wherein the dental matrix band is at least sufficiently translucent to allow light to pass through the dental matrix band.

8. A matrix band as recited in claim 1, wherein the frictional engagement surface is at least sufficiently translucent to enable light to pass through the dental matrix band.

9. A matrix band as recited in claim 1, wherein the dental matrix band is formed from plastic.

10. A matrix band as recited in claim 1, wherein the interior side is reflective such that when the matrix band is positioned around a tooth requiring restoration and light is directed through a polymerizable material, the light is reflected by the interior side of the dental matrix band back into the polymerizable material.

11. A matrix band as recited in claim 1, wherein the dental matrix band is formed from stainless steel.

12. A matrix band as recited in claim 1, wherein the dental matrix band has distinct portions such that a portion is formed from stainless steel and a portion is formed from plastic.

13. A matrix band as recited in claim 1, wherein the dental matrix band has a thickness between the exterior side and the interior side which is thinner in some portions of the band than in others.

14. A matrix band as recited in claim 1, wherein the ends are adapted for being held in a dental matrix band holder.

15. A matrix band as recited in claim 1, wherein the dental matrix band is configured such that conformance of the dental matrix band around a tooth requiring restoration renders the dental matrix band unsuitable for any subsequent use.

16. A method for preparing a tooth for restoration comprising:

obtaining a dental matrix band having opposing ends and a top edge opposite a bottom edge, the dental matrix band also having opposing sides including an interior side and an exterior side, the interior side being smooth for contact with the surfaces of a tooth requiring restoration, the exterior side having a surface which is at least partially a frictional engagement surface adapted to provide frictional engagement with a dental wedge, the frictional engagement surface of the exterior side being significantly rougher and more abrasive than the interior side, positioning the dental matrix band around a tooth requiring restoration with the interior side facing the tooth requiring restoration, and inserting a dental wedge into an interproximal space between the tooth requiring restoration and an adjacent tooth such that the dental wedge contacts the frictional engagement surface of the dental matrix band and such that the dental wedge remains in place after insertion to hold the dental matrix band stationary with respect to the tooth requiring restoration.

17. A method as recited in claim 16, wherein the frictional engagement surface of the exterior side of the dental matrix band extends from the bottom edge upward toward the top edge at least one-third of the distance between the bottom edge and the top edge.

18. A method as recited in claim 16, wherein the frictional engagement surface of the exterior side of the dental matrix band extends from the bottom edge upward toward the top edge at least one-half of the distance between the bottom edge and the top edge.

19. A method as recited in claim 16, wherein all of the surface of the exterior side of the dental matrix band is configured as a frictional engagement surface.

20. A method as recited in claim 16, wherein the frictional engagement surface extends continuously from the first end to the second end.

21. A method as recited in claim 16, wherein the frictional engagement surface extends intermittently from the first end to the second end.

22. A method as recited in claim 16, wherein the dental matrix band is at least sufficiently translucent to allow light to pass through the dental matrix band.

23. A method as recited in claim 16, wherein the frictional engagement surface is at least sufficiently translucent to enable light to pass through the dental matrix band.

24. A method as recited in claim 16, wherein the dental matrix band is formed from plastic.

25. A method as recited in claim 16, wherein the interior side of the dental matrix band is reflective such that when light is directed through a polymerizable material the light is reflected by the interior side of the dental matrix band back into the polymerizable material.

26. A method as recited in claim 16, wherein the dental matrix band is formed from stainless steel.

27. A method as recited in claim 16, wherein the dental matrix band has distinct portions such that a portion is formed from stainless steel and a portion is formed from plastic.

28. A method as recited in claim 16, wherein the dental matrix band has a thickness between the exterior side and the interior side which is thinner in some portions of the band than in others.

29. A method as recited in claim 16, wherein the dental matrix band has an elongated and slightly curved configuration such that when the ends are joined together the matrix band has a midsection which is scooped to enable the matrix band to anatomically conform to a tooth when positioned around the tooth.

30. A method as recited in claim 16, wherein the dental matrix band is preloaded in a dental matrix band holder.

31. A method as recited in claim 16, wherein the dental wedge has a translucent body.

32. A method as recited in claim 16, wherein the dental wedge has a body which has at least a portion thereof configured to provide increased frictional resistance.

33. A method as recited in claim 16, wherein the dental wedge comprises:

(a) tapered body means for insertion within the interproximal space between the two teeth, the tapered body means having a proximal end and a distal end;

(b) head means for moving the tapered body means with respect to the interproximal space between the two teeth by a dental instrument, the head means having a proximal end and a distal end; and (c) neck means for receiving a grasping end of a dental instrument to move the tapered body means with respect to the interproximal space between the two teeth, and for coupling the distal end of the head means to the proximal end of the tapered body means, said neck means comprising a circumferential periphery having five or more flat surfaces circumferentially spaced around said periphery such that said flat surfaces together define a plurality of different dripping angles and positions.

34. A method as recited in claim 16, wherein the dental wedge comprises:

(a) tapered body means for insertion within the interproximal space between the two teeth, the tapered body means having a proximal end and a distal end;

(b) head means for moving the tapered body means with respect to the interproximal space between the two teeth by a dental instrument, the head means having a proximal end and a distal end, the distal end of the head means being coupled to the proximal end of the tapered body means; and (c) a resilient, compressible cap attached to the proximal end of the head means.

35. A method for preparing a tooth for restoration comprising:

obtaining a dental matrix band having opposing ends and a top edge opposite a bottom edge, the dental matrix band also having opposing sides including an interior side and an exterior side, the interior side being smooth for contact with the surfaces of a tooth requiring restoration, the exterior side having a frictional engagement surface which extends from the bottom edge upward toward the top edge at least one-third of the distance between the bottom edge and the top edge surface, the frictional engagement surface being adapted to provide frictional engagement with a dental wedge, the frictional engagement surface of the exterior side being significantly rougher and more abrasive than the interior side, positioning the dental matrix band around a tooth requiring restoration with the interior side facing the tooth requiring restoration, and inserting a dental wedge into an interproximal space between the tooth requiring restoration and an adjacent tooth such that the dental wedge contacts the frictional engagement surface of the dental matrix band and such that the dental wedge remains in place after insertion to hold the dental matrix band stationary with respect to the tooth requiring restoration.

36. A method as recited in claim 35, wherein the frictional engagement surface of the exterior side of the dental matrix band extends from the bottom edge upward toward the top edge at least one-half of the distance between the bottom edge and the top edge.

37. A method as recited in claim 35, wherein all of the surface of the exterior side of the dental matrix band is configured as a frictional engagement surface.

38. A method as recited in claim 35, wherein the frictional engagement surface extends continuously from the first end to the second end.

39. A method as recited in claim 35, wherein the frictional engagement surface extends intermittently from the first end to the second end.

40. A method as recited in claim 35, wherein the dental matrix band is at least sufficiently translucent to allow light to pass through the dental matrix band.

41. A method as recited in claim 35, wherein the frictional engagement surface is at least sufficiently translucent to enable light to pass through the dental matrix band.

42. A method as recited in claim 35, wherein the dental matrix band is formed from plastic.

43. A method as recited in claim 35, wherein the interior side of the dental matrix band is reflective such that when light is directed through a polymerizable material the light is reflected by the interior side of the dental matrix band back into the polymerizable material.

44. A method as recited in claim 35, wherein the dental matrix band is formed from stainless steel.

45. A method as recited in claim 35, wherein the dental matrix band has distinct portions such that a portion is formed from stainless steel and a portion is formed from plastic.

46. A method as recited in claim 35, wherein the dental matrix band has a thickness between the exterior side and the interior side which is thinner in some portions of the band than in others.

47. A method as recited in claim 35, wherein the dental matrix band has an elongated and slightly curved configuration such that when the ends are joined together the matrix band has a midsection which is scooped to enable the matrix band to anatomically conform to a tooth when positioned around the tooth.

48. A method as recited in claim 35, wherein the dental matrix band is preloaded in a dental matrix band holder.

49. A method as recited in claim 35, wherein the dental wedge has a translucent body.

50. A method as recited in claim 35, wherein the dental wedge has a body which has at least a portion thereof configured to provide increased frictional resistance.

* * * * *

UNITED STATES PATENT AND TRADEMARK OFFICE
CERTIFICATE OF CORRECTION

PATENT NO. : 6,234,793 B1  
DATED : May 22, 2001  
INVENTOR(S) : Steven J. Brattesani and Dan E. Fischer Page 1 of 1

It is certified that error appears in the above-identified patent and that said Letters Patent is hereby corrected as shown below:

Column 6,  
Line 4, change "an" to -- a --

Column 20,  
Line 19, after "embodiments" insert -- . --

Column 21,  
Lines 21 and 28, change "comers" to -- corners --  
Line 33, change "provide" to -- provided --

Signed and Sealed this

Sixteenth Day of April, 2002

Attest:

JAMES E. ROGAN  
*Director of the United States Patent and Trademark Office*

*Attesting Officer*